US011020450B2

(12) United States Patent
Han et al.

(10) Patent No.: US 11,020,450 B2
(45) Date of Patent: Jun. 1, 2021

(54) MEDICAL USE OF CREG PROTEIN

(71) Applicant: GENERAL HOSPITAL OF CHINESE PLA NORTHERN THEATER COMMAND, Shenyang (CN)

(72) Inventors: Yaling Han, Shenyang (CN); Chenghui Yan, Shenyang (CN); Dan Liu, Shenyang (CN); Xiaoxiang Tian, Shenyang (CN); Yang Li, Shenyang (CN); Xiaolin Zhang, Shenyang (CN); Haixu Song, Shenyang (CN); Meili Liu, Shenyang (CN)

(73) Assignee: GENERAL HOSPITAL OF CHINESE PLA NORTHERN THEATER COMMAND, Shenyang (CN)

( * ) Notice: Subject to any disclaimer, the term of this patent is extended or adjusted under 35 U.S.C. 154(b) by 184 days.

(21) Appl. No.: 15/748,621

(22) PCT Filed: Apr. 19, 2016

(86) PCT No.: PCT/CN2016/079633
§ 371 (c)(1),
(2) Date: Jan. 29, 2018

(87) PCT Pub. No.: WO2017/016244
PCT Pub. Date: Feb. 2, 2017

(65) Prior Publication Data
US 2019/0076502 A1 Mar. 14, 2019

(30) Foreign Application Priority Data

Jul. 30, 2015 (CN) .......................... 201510454704.0
Jul. 30, 2015 (CN) .......................... 201510460110.0

(51) Int. Cl.
*A61K 38/00* (2006.01)
*C07K 14/00* (2006.01)
*A61K 38/17* (2006.01)
*G01N 33/68* (2006.01)
*C07K 14/47* (2006.01)
*A01K 67/027* (2006.01)
*A61P 9/10* (2006.01)
*C12N 15/52* (2006.01)
*A61K 48/00* (2006.01)

(52) U.S. Cl.
CPC .......... *A61K 38/17* (2013.01); *A01K 67/0276* (2013.01); *A61P 9/10* (2018.01); *C07K 14/4702* (2013.01); *C12N 15/52* (2013.01); *G01N 33/68* (2013.01); *G01N 33/6893* (2013.01); *A01K 2217/077* (2013.01); *A01K 2227/105* (2013.01); *A01K 2267/0375* (2013.01); *A61K 48/00* (2013.01); *G01N 2800/324* (2013.01); *G01N 2800/325* (2013.01)

(58) Field of Classification Search
None
See application file for complete search history.

(56) References Cited

FOREIGN PATENT DOCUMENTS

| CN | 101519663 A | * 9/2009 |
| CN | 105056208 A | 11/2015 |
| CN | 105194651 A | 12/2015 |

OTHER PUBLICATIONS

Zhang et al. Transplantation of cellular repressor of E1A-stimulated gene modified embryonic stem cells improves heart function postmyocardial infarction. Heart, vol. 99, Supp. Suppl. 3, pp. A19. Abstract No. GW24-e1273 (Aug. 2013). (Year: 2013).*
Song et al. Effect of cellular repressor of E1A stimulated genes (CREG1) on cardiac function injury induced by angiotensin II in mice. Med. J. Chin PLA, vol. 40, No. 1:16-21 (Jan. 1, 2015). (Year: 2015).*
Yang et al. Cellular repressor of E1A-stimulated genes protects against angiotensin II-induced hypertension and vascular remodeling via p38MAPK-mediated regulation of the renin-angiotensin system. Abstract. J. Amer. Coll. Card. , vol. 64/16. Suppl 1, pp. C14-C15 GW25-e1138 (Oct. 21, 2014). (Year: 2014).*
Yan et al. Cellular repressor of E1A-stimulated genes protects from myocardial ischemia/reperfusion injury by regulating myocardial autophagy and apoptosis. Abstract. Circulation vol. 132, No. Suppl. 3pp. 17066 (Nov. 10, 2015). (Year: 2015).*
Schahs et al. The two N-glycans of murine Cellular Repressor of E1A-stimulated Genes (CREG) are both engaged in lysosomal sorting of the protein. Abstract. Glycoconjugate Journal, vol. 28, No. 5, pp. 275-276. Abstract No. 203 (Jul. 2011). (Year: 2011).*
Sacher et al. The crystal structure of CREG, a secreted glycoprotein involved in cellular growth and differentiation. PNAS, vol. 102, No. 51 (Dec. 2005). (Year: 2005).*
Bhattacharya et al. (Impact of genetic variation on three dimensional structure and function of proteins; PLOS One 12(3): e0171355, pp. 1-22 (Mar. 2017). (Year: 2017).*
Tokuriki et al., Stability effects of mutations and protein evolvability; Current Opinion in Structural Biology, 19:596-604 (2009). (Year: 2009).*

(Continued)

*Primary Examiner* — Elizabeth C. Kemmerer
*Assistant Examiner* — Regina M DeBerry
(74) *Attorney, Agent, or Firm* — Kilpatrick Townsend & Stockton LLP

(57) ABSTRACT

The present invention relates to a medical use of Cellular Repressor of E1A-stimulated Genes (CREG), in particular to a use of CREG protein or active fragment thereof in manufacture of a medicament for preventing and/or treating myocardial infarction, a use in manufacture of a medicament for preventing and/or treating ventricular remodeling after myocardial infarction and heart failure after myocardial infarction, a use in manufacture of a medicament for prevention and/or treatment of myocardial ischemia-reperfusion injury, a use in manufacture of a medicament for prevention and/or treatment of salt-sensitive hypertensive myocardial fibrosis.

3 Claims, 12 Drawing Sheets
Specification includes a Sequence Listing.

(56) References Cited

OTHER PUBLICATIONS

Bian et al. Cellular repressor of E1A-stimulated genes attenuates cardiac hypertrophy and fibrosis. J. Cell. Mol. Med. vol. 13/No. 7: 1302-1313 (2009). (Year: 2009).*

Jian et al. Cellular repressor of E1A-stimulated genes improves heart function in a mouse model of MI. Abstract, Heart, vol. 101, Suppl. 1, pp. A18-A19 (Jan. 2015). (Year: 2015).*

CN101519663A (Yan et al. English Translation of document CN101519663A). Recombinant CREG protein and application thereof. pp. 1-7; (document published Sep. 2, 2009). (Year: 2009).*

Song et al. Effect of CREG 1 Protein on Cardiac Function Injury Induced by Angiotensis II in Mice. Medical Journal of China PLA, vol. 40, No. 1:16-21; Jan. 1, 2015 (English Translation). (Year: 2015).*

International Search Report issued in connection with corresponding International Application No. PCT/CN2016/079633, dated Jul. 25, 2016, 1 page.

Liang, Zhenyang et al., "The Expression of Serum CREG Protein in the Early Period of Acute Myocardial Infarction", Progress in Modern Biomedicine, vol. 23, No. 23, Dec. 31, 2011 (Dec. 31, 2011), pp. 4468-4471.

Li, Jie et al., "The Protective Effect of Cellular Repressor of E1A Stimulated Genes Modified Embryonic Stem Cell Transplantation on Cardiac Function of Myocardial Infarction Mice", Chinese Circulation Journal, vol. 26, No. Supplement, Aug. 31, 2011 (Aug. 31, 2011), p. 77.

Liu, Meili et al., "CREG Protein participated Cardiac Remodeling in Salt Sensitive Hypertensive Rats Induced by High-Salt", Chinese Circulation Journal, vol. 30, No. Supplement, Aug. 30, 2015 (Aug. 30, 2015), p. 13.

\* cited by examiner

MEDICAL USE OF CREG PROTEIN

CROSS-REFERENCE TO RELATED APPLICATIONS

This application is a national stage application under 35 U.S.C. § 371 of International Patent Application No. PCT/CN2016/079633, filed Apr. 19, 2016, which claims priority to Chinese Application No. 201510454704.0, filed Jul. 30, 2015, and Chinese Application No. 201510460110.0, filed Jul. 30, 2015 the disclosures of which are hereby incorporated by reference for all purposes in their entireties.

REFERENCE TO A SEQUENCE LISTING

The Substitute Sequence Listing written in file SubstituteSequenceListing_089317-001600US-1076035.txt created on Oct. 8, 2018, 2,529 bytes, machine format IBM-PC, MS-Windows operating system, is hereby incorporated by reference in its entirety for all purposes.

TECHNICAL FIELD

The present invention relates to the medical use of Cellular Repressor of E1A-stimulated Genes (CREG), in particular to uses of CREG protein or an active fragment thereof for preparing a medicament for prevention and/or treatment of myocardial infarction, for preparing a medicament for prevention and/or treatment of ventricular remodeling and heart failure after myocardial infarction, for preparing a medicament for prevention and/or treatment of myocardial ischemia-reperfusion injury, for preparing a medicament for prevention and/or treatment of salt-sensitive myocardial fibrosis in hypertension.

BACKGROUND ART

Coronary heart disease (CHD) is one of the most serious diseases that threaten human health and life. Acute myocardial infarction (AMI) is the main manifestation of CHD, AMI and heart failure post-infarction are the major causes of CHD deaths. The 2013 China Cardiovascular Disease Research Report has pointed out that there are at least 500,000 new AMIs each year in China, and about 2.5 million patients are currently suffering from myocardial infarction. AMI becomes a major public health problem in China due to its high morbidity rate, high disability rate and high mortality rate. Myocardial ischemia during AMI is the main cause of myocardial injury and necrosis. Within a few seconds of myocardial ischemia, cardiomyocyte membrane permeability increases, intracellular ultrastructure changes, swell and edema of organelles and leakage of cytosol occur, which finally lead to death of cardiomyocytes. Cardiomyocytes are terminally differentiated cells that lack the ability to proliferate and differentiate. Therefore, the dead cardiomyocytes cannot be supplemented by differentiation of other cardiomyocytes, and only can be filled by cardiac interstitial fibroblasts, so that progressive remodeling of ventricle occurs, which eventually causes heart failure and death in AMI patients. Currently, the treatment of AMI mainly includes drug thrombolysis, coronary artery intervention, coronary artery bypass surgery, although these measures can alleviate the symptoms of myocardial ischemia in patients to some extent, they can hardly combat myocardial injury and heart failure after AMI. Therefore, the search for drugs against cardiomyocyte damage that fundamentally inhibit heart failure after AMI, and play an important roles in the treatment and prognosis improvement of prognosis of AMI.

Myocardial ischemia reperfusion (MIR) injury refers to injury and dysfunction after recovery of blood perfusion in myocardial tissue after a long period of ischemia, which are more obvious and serious than before reperfusion, including decreased systolic function, reduced coronary arterial blood flow and changed vascular reactivity. At present, the current treatment of AMI mainly includes drug thrombolysis, coronary artery intervention, coronary artery bypass surgery, etc., but when these ways alleviate the symptoms of ischemia, they may also cause myocardial reperfusion injury. Studies have shown that the mechanisms of MIR injury include oxygen free radicals, neutrophil infiltration, nitric oxide production, calcium overload and so on. According to these mechanisms, some treatments are used such as elimination of free radicals, "post-ischemic adaptation" treatment, inhibition of $Na^+/Ca^{2+}$ ion exchange. However, each way has shortcomings and deficiencies, therefore, how to better prevent and treat reperfusion injury is an urgent problem to be solved.

Salt is an important predisposing factor for hypertension, and salt sensitivity problem arises due to different blood pressure responses to salt stress or salt restriction among individuals in the population. According to statistics, hypertension patients account for more than 20% of the total population in China, and over 50% of them are salt-sensitive hypertension, and salt-sensitive hypertension has been listed as an important independent risk factor for cardiovascular diseases. Epidemiological studies suggest that the incidence rate and mortality rate for cardiovascular events are significantly higher in the salt-sensitive hypertensive patients than non-salt-sensitive hypertensive patients. Cardiac fibrosis is one of the important pathological changes of cardiac remodeling in hypertension and an important pathophysiological basis of cardiovascular events in hypertension. Studies have shown that hypertensive myocardial fibrosis is accompanied by infiltration of the periventricular and interstitial inflammatory cells around coronary arteries, and inflammatory responses play an important regulatory role in myocardial fibrosis remodeling. However, the specific regulatory mechanisms are still not fully understood. Therefore, in order to combat salt-sensitive hypertensive myocardial fibrosis, how to better prevent and treat inflammation of myocardium is an urgent problem to be solved.

The CREG gene is a cell differentiation regulatory gene and is cloned from the cDNA library of endometrial cancer Hela cell in 1998 by Professor Gill of the Harvard Medical School (Veal E, Mol Cell Biol, 1998; 18 (9): 5032-5041). CREG protein is a small molecular weight secreted glycoprotein that is widely expressed in mature tissue cells and has the function of maintaining the differentiation of tissues and cells. CREG proteins are predominantly located in perinuclear Golgi complexes and lysosomes, and CREG are involved in the transport of lysosomal enzymes and the endocytosis of extracellular factors (Schahs P, Exp Cell Res, 2008, 314 (16): 3036-3047; Kowalewski-Nimmerfall E, Biochim Biophys Acta, 2014, 1843 (12): 2900-2912). A large number of studies have shown that CREG proteins are involved in the occurrence and progression of many cardiovascular diseases. However, the effects of CREG proteins on myocardial infarction, ventricular remodeling and heart failure after myocardial infarction, myocardial ischemia-reperfusion injury, and myocardial fibrosis in salt-sensitive hypertension remains unclear.

Content of the Invention

Surprisingly, the inventors of the present invention found that CREG protein expression were significantly decreased in cardiac muscle tissue of mice after AMI, the CREG heterozygous (CREG$^{+/-}$) mice showed significantly increase in mortality rate after AMI, significantly decrease in cardiac function indicators, left ventricular ejection fraction (EF %) and left ventricular shortening fraction (FS %), increase in degree of myocardial fibrosis, and more obvious ventricular remodeling; and the exogenous supplementation of recombinant CREG protein to wild-type mice (CREG$^{+/+}$) with AMI could significantly improve the cardiac function after AMI, significantly increase EF % and FS % values, alleviate degree of myocardial fibrosis, and significantly improve ventricular remodeling, which indicated that exogenous supplementation of CREG protein could be used to prevent or treat AMI and heart failure and/or ventricular remodeling after AMI. The present invention is based on the above findings.

The first aspect of the invention relates to a use of a CREG protein or an active fragment thereof in the manufacture of a medicament, wherein the medicament is used for one or more of the following items:

1) prevention and/or treatment of acute myocardial infarction;

2) prevention and/or treatment of heart failure after acute myocardial infarction;

3) prevention and/or treatment of ventricular remodeling after acute myocardial infarction;

4) improvement of cardiac function after acute myocardial infarction.

The invention also relates to a use of a nucleic acid molecule encoding a CREG protein or an active fragment thereof, a recombinant vector or a recombinant cell expressing a CREG protein or an active fragment thereof, in the manufacture of a medicament, wherein the medicament is used for one or more of the following items:

1) prevention and/or treatment of acute myocardial infarction;

2) prevention and/or treatment of heart failure after acute myocardial infarction;

3) prevention and/or treatment of ventricular remodeling after acute myocardial infarction;

4) improvement of cardiac function after acute myocardial infarction.

In an embodiment of the invention, the recombinant vector contains a nucleic acid molecule encoding a CREG protein or an active fragment thereof.

The present invention also relates to a use of a reagent capable of promoting the up-regulation of expression of a CREG protein or an active fragment thereof in the manufacture of a medicament, wherein the medicament is used for one or more of the following items:

1) prevention and/or treatment of acute myocardial infarction;

2) prevention and/or treatment of heart failure after acute myocardial infarction;

3) prevention and/or treatment of ventricular remodeling after acute myocardial infarction;

4) improvement of cardiac function after acute myocardial infarction.

The present invention also relates to a use of a reagent that detects the expression level of a CREG protein or an active fragment thereof in the manufacture of a kit, in which the kit is used for one or more of the following items:

1) diagnosis and/or risk assessment of acute myocardial infarction;

2) diagnosis and/or risk assessment of heart failure after acute myocardial infarction;

3) diagnosis and/or risk assessment of ventricular remodeling after acute myocardial infarction;

4) prediction and/or assessment of cardiac function after acute myocardial infarction.

The invention also relates to a use of a CREG protein or an active fragment thereof in screening a medicament for prevention and/or treatment of acute myocardial infarction, heart failure after acute myocardial infarction, and/or ventricular remodeling after acute myocardial infarction.

In an embodiment of the present invention, a CREG protein or an active fragment thereof can be used as a target protein in screening a medicament for prevention and/or treatment of acute myocardial infarction, heart failure after acute myocardial infarction and/or ventricular remodeling after acute myocardial infarction; for example, a reagent capable of promoting the up-regulation of expression of a CREG protein or an active fragments thereof can be used as a medicament for prevention and/or treatment of acute myocardial infarction, heart failure after acute myocardial infarction and/or ventricular remodeling after acute myocardial infarction.

The present invention also relates to a composition comprising a CREG protein or an active fragment thereof, a nucleic acid molecule encoding a CREG protein or an active fragment thereof, a recombinant vector or recombinant cell expressing a CREG protein or an active fragment thereof, or a reagent capable of promoting the up-regulation of expression of a CREG protein or an active fragment thereof, and optionally a pharmaceutically acceptable carrier or excipient, in which the composition is used for one or more of the following items:

1) prevention and/or treatment of acute myocardial infarction;

2) prevention and/or treatment of heart failure after acute myocardial infarction;

3) prevention and/or treatment of ventricular remodeling after acute myocardial infarction;

4) improvement of cardiac function after acute myocardial infarction.

The present invention also relates to a kit comprising a reagents for detection of expression level of a CREG protein or an active fragment thereof, in which the kit is used for one or more of the following items:

1) diagnosis and/or risk assessment of acute myocardial infarction;

2) diagnosis and/or risk assessment of heart failure after acute myocardial infarction;

3) diagnosis and/or risk assessment of ventricular remodeling after acute myocardial infarction;

4) prediction and/or assessment of cardiac function after acute myocardial infarction.

In the present invention, a large number of experiments showed that, during myocardial ischemia-reperfusion in CREG$^{+/+}$ mice, the CREG protein expression significantly decreased. Compared with CREG$^{+/+}$ mice, the cardiac function of CREG$^{+/-}$ mice was significantly decreased after 28 days of myocardial ischemia-reperfusion, while the cardiac function was remarkably improved when a recombinant CREG protein was exogenously administered. It was further found that the autophagosomes were accumulated, the number of autolysosome was reduced and the autophagy function decreased in myocardium of CREG$^{+/-}$ mice during myocardial ischemia-reperfusion, which resulted in the increase of cardiomyocyte death and the decrease of cardiac function. After exogenous administration of recombinant CREG protein, the autophagy function was significantly improved, and cardiomyocyte death decreased. It can be seen that the exogenous recombinant CREG protein can prevent cardiac dysfunction caused by myocardial ischemia-reperfusion via regulating the autolysosome pathway, and thus the present invention was completed.

The second aspect of the present invention relates to a use of a CREG protein or an active fragment thereof in the manufacture of a medicament for prevention and/or treatment of myocardial ischemia-reperfusion injury.

The present invention also relates to a use of a recombinant vector or recombinant cell expressing a CREG protein or an active fragment thereof in the manufacture of a medicament for prevention and/or treatment of myocardial ischemia-reperfusion injury; wherein, the recombinant cell contains a recombinant vector that expresses the CREG protein or active fragment thereof, and the recombinant vector comprises a nucleotide sequence encoding the CREG protein or active fragment thereof.

In an embodiment of the invention, the recombinant vector is a recombinant adenovirus vector.

The present invention also relates to a use of a reagent capable of promoting the up-regulation of expression of a CREG protein or an active fragment thereof in the manufacture of a medicament for prevention and/or treatment of myocardial ischemia-reperfusion injury.

The present invention also relates to a use of a CREG protein or an active fragment thereof in screening a medicament for prevention and/or treatment of myocardial ischemia-reperfusion injury.

The invention also relates to a composition comprising a CREG protein or an active fragment thereof, a recombinant vector or recombinant cell expressing a CREG protein or an active fragment thereof, a reagent capable of promoting the up-regulation of expression of a CREG protein or an active fragment thereof, and optionally a pharmaceutically acceptable carrier or excipient, in which the composition is used for prevention and/or treatment of myocardial ischemia-reperfusion injury.

The present invention also relates to a use of a CREG protein or an active fragment thereof to combat myocardial injury in myocardial ischemia-reperfusion in vivo or in vitro.

In the present invention, a large number of experiments showed that Dahl salt-sensitive rats exhibited significantly increased blood pressure and heart weight after high salt stress, and significant myocardial fibrosis injury appeared at the same time; in this procedure, a large number of inflammatory cells were infiltrated, and CREG protein was significantly down-regulated. After the Dahl rats of the high salt stress group were administrated with exogenous recombinant CREG protein, ratio of heart weight/body weight and ratio of heart weight/tibia length were effectively inhibited, myocardial interstitial and perivascular fibrosis was significantly reduced, and macrophage infiltration decreased significantly. It can be seen that the exogenous recombinant CREG protein can effectively improve salt-sensitive hypertensive myocardial fibrosis by combating inflammatory cell infiltration, thus completing the present invention.

The third aspect of the invention relates to a use of a CREG protein or an active fragment thereof in the manufacture of a medicament for prevention and/or treatment of salt-sensitive hypertensive myocardial fibrosis.

The invention also relates to a use of a nucleic acid molecule encoding a CREG protein or an active fragment thereof, a recombinant vector or recombinant cell expressing a CREG protein or an active fragment thereof in the manufacture of a medicament for the prevention and/or treatment of salt-sensitive hypertensive myocardial fibrosis injury; wherein, the recombinant cell comprises a recombinant vector expressing the CREG protein or active fragment thereof, and the recombinant vector comprises a nucleotide sequence encoding the CREG protein or active fragment thereof.

The present invention also relates to a use of a reagent capable of promoting the up-regulation of expression of a CREG protein or an active fragment thereof in the manufacture of a medicament for prevention and/or treatment of salt-sensitive hypertensive myocardial fibrosis.

The present invention also relates to a use of a CREG protein or an active fragment thereof in screening a medicament for prevention and/or treatment of salt-sensitive hypertensive myocardial fibrosis.

In an embodiment of the present invention, a CREG protein or an active fragment thereof may be used as a target protein in screening a medicament for prevention and/or treatment of salt-sensitive hypertensive myocardial fibrosis; for example, a reagent capable of promoting the up-regulation of expression of a CREG protein or an active fragment thereof can be used as a medicament for prevention and/or treatment of salt-sensitive hypertensive myocardial fibrosis.

The invention also relates to a composition comprising a CREG protein or an active fragment thereof, a recombinant vector or recombinant cell expressing a CREG protein or an active fragment thereof, a reagent capable of promoting the up-regulation of expression of a CREG protein or an active fragment thereof, and optionally a pharmaceutically acceptable carrier or excipient, in which the composition is used for the prevention and/or treatment of salt-sensitive hypertensive myocardial fibrosis.

The invention also relates to a use of a CREG protein or an active fragment thereof in combating injury of myocardial fibroblasts in salt-sensitive hypertensive myocardial fibrosis in vivo or in vitro.

In the present invention, the CREG protein is a recombinant CREG protein which is derived from mammals, particularly from human. In an exemplary embodiment of the invention, the GenBank number of the CREG protein is NP_003842.1. In an exemplary embodiment of the invention, the GenBank number of the CREG gene is NM_003851.2.

In the present invention, the active fragment of CREG protein refers to a fragment having the function of CREG protein, which may be a part of CREG protein or a fragment obtained by deleting, adding or replacing the amino acid sequence of CREG protein; the methods for obtaining the active fragment of CREG proteins are well known in the art; for example, the active fragment is a fragment comprising the portion of CREG protein bound to ligand or receptor, or a fragment that retains the function of CREG protein after deletion, addition or substitution of amino acids. It is known to those skilled in the art that there are some key amino acids in the CREG protein which are closely related to the activity of protein and affect the activity of protein after being mutated. For example, when the lysines at the 136th and 137th positions of the CREG protein were mutated to alanine, or the amino acids at the 141th to the 144th positions of the CREG protein were deleted in mutation, the activity and function of protein would be changed (Sacher M, PNAS, 2005; 102 (51): 18326-18331). Those skilled in the art can avoid these above-mentioned positions that may affect the activity as needed, and make modifications, such as deletion, addition or substitution, at other positions, so that the modified CREG protein still has the activity or function of the CREG protein.

In the present invention, the methods for obtaining a recombinant CREG protein or an active fragment thereof are known in the art, for example, which can be obtained by constructing a gene of CREG protein or active fragment thereof into an expression vector, then transferring the expression vector into a cell for expression, and performing purification.

In an embodiment of the invention, the CREG protein or active fragment thereof is a glycosylated protein or a non-glycosylated protein.

In the present invention, the glycosylated CREG protein refers to a CREG protein which amino acids at positions 160, 193 and 216 have glycosylation modification.

In the present invention, the non-glycosylated CREG protein refers to a CREG protein which amino acids are not glycosylated.

It is well known to those skilled in the art that glycosylation may occur when a protein is expressed in eukaryotic cells (e.g, yeast cells, mammalian cells), while glycosylation usually may not occur during expression in prokaryotic cells. The glycosylated CREG protein and the non-glycosylated CREG protein have similar biological activity and function.

In the present invention, the acute myocardial infarction (AMI) has a well-known meaning in the art and refers to a series of pathological processes of coronary artery such as myocardial injury and even necrosis caused by acute and persistent ischemia and hypoxia.

In the present invention, the heart failure after acute myocardial infarction has a well-known meaning in the art and refers to a syndrome of cardiac insufficiency caused by acute myocardial infarction, which mainly refers to a manifestation caused by a decrease in cardiac contractility, in which cardiac output can not meet the requirements of organisms' metabolism, hypoperfusion occurs in organs and tissues, and congestion appears in pulmonary and (or) systemic circulation at the same time.

In the present invention, the ventricular remodeling after acute myocardial infarction has the meaning well-known in the art and refers to myocardial infarction-induced or myocardial infarction-related ventricular remodeling. The ventricular remodeling mainly refers to left ventricular remodeling, including thinning and stretching of myocardium of ventricular wall and generation of "bulging" at infarction region, that is, a process comprising expansion at infarction region and reactive hypertrophy and elongation of ventricular myocardium at non-infarction region, which result in progressive expansion and deformation of left ventricular, accompanied with a decrease of cardiac function.

In the present invention, the prevention and/or treatment of acute myocardial infarction or heart failure after acute myocardial infarction refers to a pathological change comprising: inhibiting or reducing the occurrence of heart failure after myocardial infarction, inhibiting or slowing the progress of heart failure after myocardial infarction, and/or reversing heart failure after myocardial infarction.

In the present invention, the prevention and/or treatment of acute myocardial infarction or ventricular remodeling after acute myocardial infarction refers to a pathological change comprising: inhibiting or reducing the occurrence of ventricular remodeling after myocardial infarction, inhibiting or slowing the progress of ventricular remodeling after myocardial infarction, and/or reversing ventricular remodeling after myocardial infarction.

In the present invention, the use of detecting expression level of CREG protein or active fragment thereof in diagnosis or risk assessment or prediction and/or assessment refers to that when the expression level of CREG protein or active fragment thereof in a blood, tissue or cell is lower than the reference value, acute myocardial infarction, heart failure after acute myocardial infarction, ventricular remodeling after acute myocardial infarction can be can be diagnosed, or high risk of acute myocardial infarction, heart failure after acute myocardial infarction, ventricular weight after acute myocardial infarction can be assessed, or poor cardiac function can be predicted or assessed.

In the present invention, the myocardial ischemia-reperfusion injury refers to worsening condition after recovery of reperfusion of ischemic myocardium which causes further damage of ultrastructure, function, metabolism and electrophysiology. It is a further injury on the basis of ischemic injury, for example, reperfusion injection may occur after during cardiac surgery, coronary artery bypass surgery, recanalization of organ blood supply after infarction (e.g., recanalization after myocardial infarction), organ transplant (e.g., heart transplant) and shock organ (such as heart).

In the present invention, the prevention and/or treatment of myocardial ischemia-reperfusion injury refers to the inhibition or alleviation of the occurrence and progression of myocardial ischemia-reperfusion injury and/or the reversal of its pathological changes, for example, which includes reduction of myocardial necrosis area, improvement cardiac function, reduction of myocardial apoptosis, activation of cardiac autophagy and so on.

In the present invention, the salt-sensitive hypertensive myocardial fibrosis has a well-known meaning in the art and refers to ventricular remodeling induced after salt-sensitive hypertension or related to salt-sensitive hypertension; the ventricular remodeling mainly refers to left ventricular remodeling, including a pathological process in which myocardial interstitial and/or coronary perivascular deposition of a large amount of collagen, leading to ventricular concentric hypertrophy.

In the present invention, the prevention and/or treatment of salt-sensitive hypertensive myocardial fibrosis refers to inhibiting or slowing the occurrence, progression, and/or reversal of pathological changes of myocardial fibrosis after salt-sensitive hypertension, for example, including slowing down myocardial inflammatory response, reducing collagen deposition, reducing myocardial necrosis area and so on.

In the present invention, the vector is, for example, a prokaryotic expression vector, an eukaryotic expression vector, a phage vector or a viral vector. The prokaryotic expression vector is, for example, a PET vector or a PGEX vector, and the eukaryotic expression vector is, for example, pcDNA3.1(+), pcDNA3.1(+)-His/Myc and pEGFP-C1, and the viral vector is, for example, an adenovirus vector or a lentiviral vector.

In the embodiment of the present invention, the recombinant adenovirus vector is a type 5 human adenovirus, Ad5-CREG, which was deposited at the China Center for Type Culture Collection (CCTCC, Wuhan, Wuhan University) on Jan. 2, 2008, Accession No. CCTCC-V200801. The deposit information is disclosed in Chinese patent publication CN 101475961A.

In the present invention, a host cell transfected with a specific nucleic acid or vector can be obtained by any kind of transfection method known in the art. For example, the nucleic acid can be introduced into a cell by a transfection reagent, such as FuGENE®6 and Lipofectamine 2000; or the nucleic acid can be introduced into a cell by an adenovirus vector.

In the present invention, the cell may be a prokaryotic or eukaryotic cell. The eukaryotic cell is, for example, a mammalian cell. The cell can be obtained by introducing a recombinant vector into a prokaryotic cell or eukaryotic cell.

In the present invention, the prokaryotic cell may be *Escherichia coli* DH5α, JM109, Top10 and the like, and the eukaryotic cell may be, for example, CHO cell, 293T cell, vascular smooth muscle cell and the like. In the present invention, for example, the mammal may be a rat, a mouse, a dog, a miniature pig, a monkey, a human or the like.

In the present invention, the host cell transfected with a particular nucleic acid or vector can be obtained by using any transfection methods known in the art, for example, by introducing the nucleic acid into the cell by electroporation or microinjection; or by using a lipofectin reagent, such as FuGENE 6, X-tremeGENE, and LipofectAmine; or by introducing the nucleic acid into the cell via an appropriate viral vector based on retroviruses, lentiviruses, adenoviruses and adeno-associated viruses.

In the present invention, the expression level of CREG protein or active fragment thereof can be detected by a method known in the art, for example, by amplifying mRNA of CREG using polymerase chain reaction and performing quantitative reaction, or by detecting CREG protein expression level using Western blot.

In the present invention, the expression level of the protein means the level of mRNA or the level of protein.

In the present invention, the up-regulation/down-regulation of expression of protein in tissue/cell means that the level of protein or mRNA in the tissue/cell is increased or decreased by at least 20%, 30%, 40%, 50%, 60%, 70%, 80%, 90%, 100%, or increased by more than 100%. The up-regulation or down-regulation is compared to the non-intervened tissue/cell (e.g., a tissue/cell transfected with a control vector).

In the present invention, the reagent capable of promoting the up-regulation of expression of CREG protein or active fragment thereof is known in the art, for example, is a regulating molecule, such as promoter, enhancer and the like, capable of increasing the expression level of CREG protein.

In the present invention, the CREG protein or active fragment thereof can be used as a target protein in screening for a medicament capable of preventing and/or treating acute myocardial infarction, heart failure after acute myocardial infarction and/or ventricular remodeling after acute myocardial infarction, myocardial ischemia-reperfusion injury, salt-sensitive hypertensive myocardial fibrosis.

(C-D) With application of myocardial ischemia-reperfusion, CREG protein expression levels in myocardium at different time points were detected by Western blot in CREG$^{+/+}$ mice, reCREG$^{+/+}$ mice, and CREG$^{+/-}$ mice.

Figure 6:
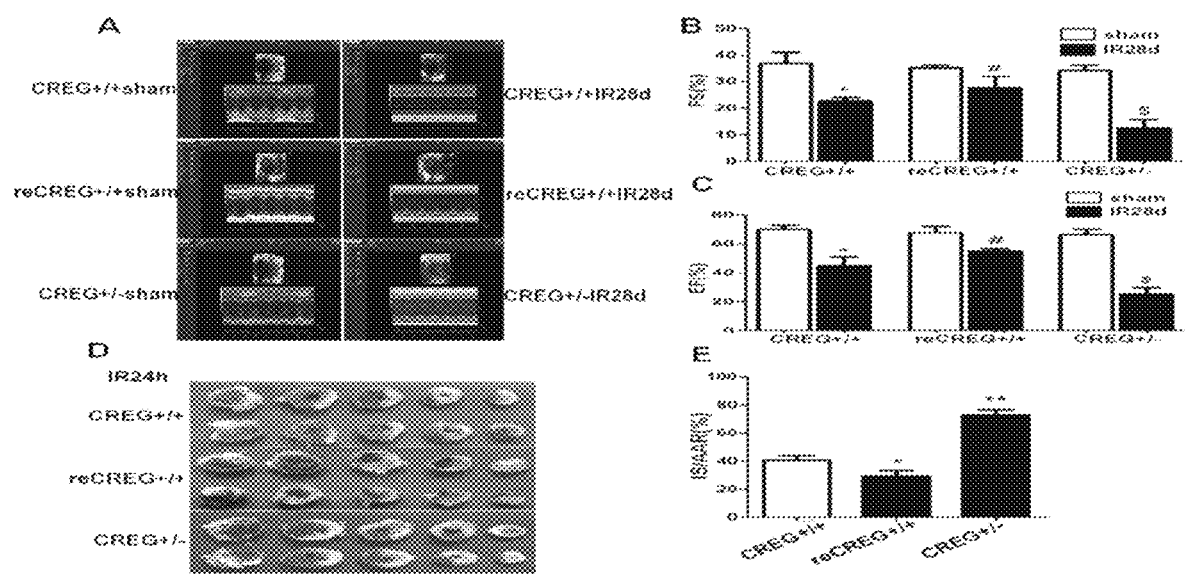

FIG. 6: Evaluation of cardiac function by Small Animal ultrasonography and TTC staining in CREG$^{+/+}$ mice, reCREG$^{+/+}$ mice, and CREG$^{+/-}$ mice after myocardial ischemia-reperfusion;

(A-C) Comparison of cardiac function at 28 days after myocardial ischemia-reperfusion in the mice of three groups by Small Animal ultrasonography. EF refers to left ventricular ejection fraction, FS refers to shortening fraction of left ventricular;

(D-E) Evaluation of myocardial injury at 24 h after myocardial ischemia-reperfusion in the mice of three groups by TTC staining (IS/AAR refers to a ratio of myocardial necrosis area to myocardial ischemia area).

Figure 7:
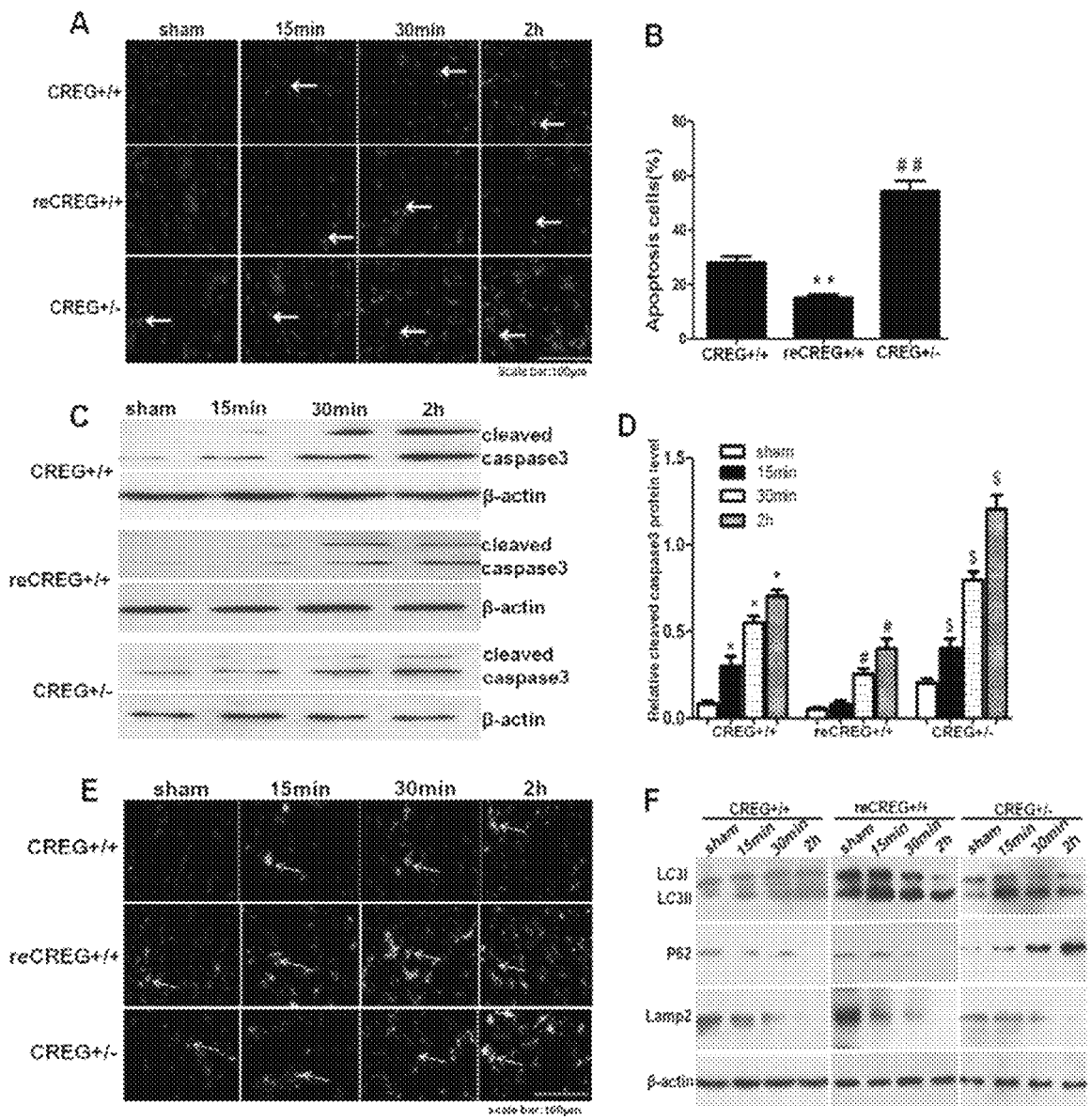

FIG. 7: Evaluation of cardiomyocyte apoptosis and autophagy protein expression by Immunofluorescence staining and Western blot in CREG$^{+/+}$ mice, reCREG$^{+/+}$ mice and CREG$^{+/-}$ mice after myocardial ischemia-reperfusion;

(A-B) cardiomyocyte apoptosis in the mice of three groups was detected by Tunel staining;

(C-D) Expression of myocardial apoptosis protein cleaved caspase 3 in myocardium was detected by Western blot in the mice of three groups;

(E) Expression of autophagy protein LC3B in myocardium was detected by Immunofluorescence staining in the mice of three groups;

(F) Expression of autophagy protein in myocardium was detected by Western blot in the mice of three groups.

Figure 8:
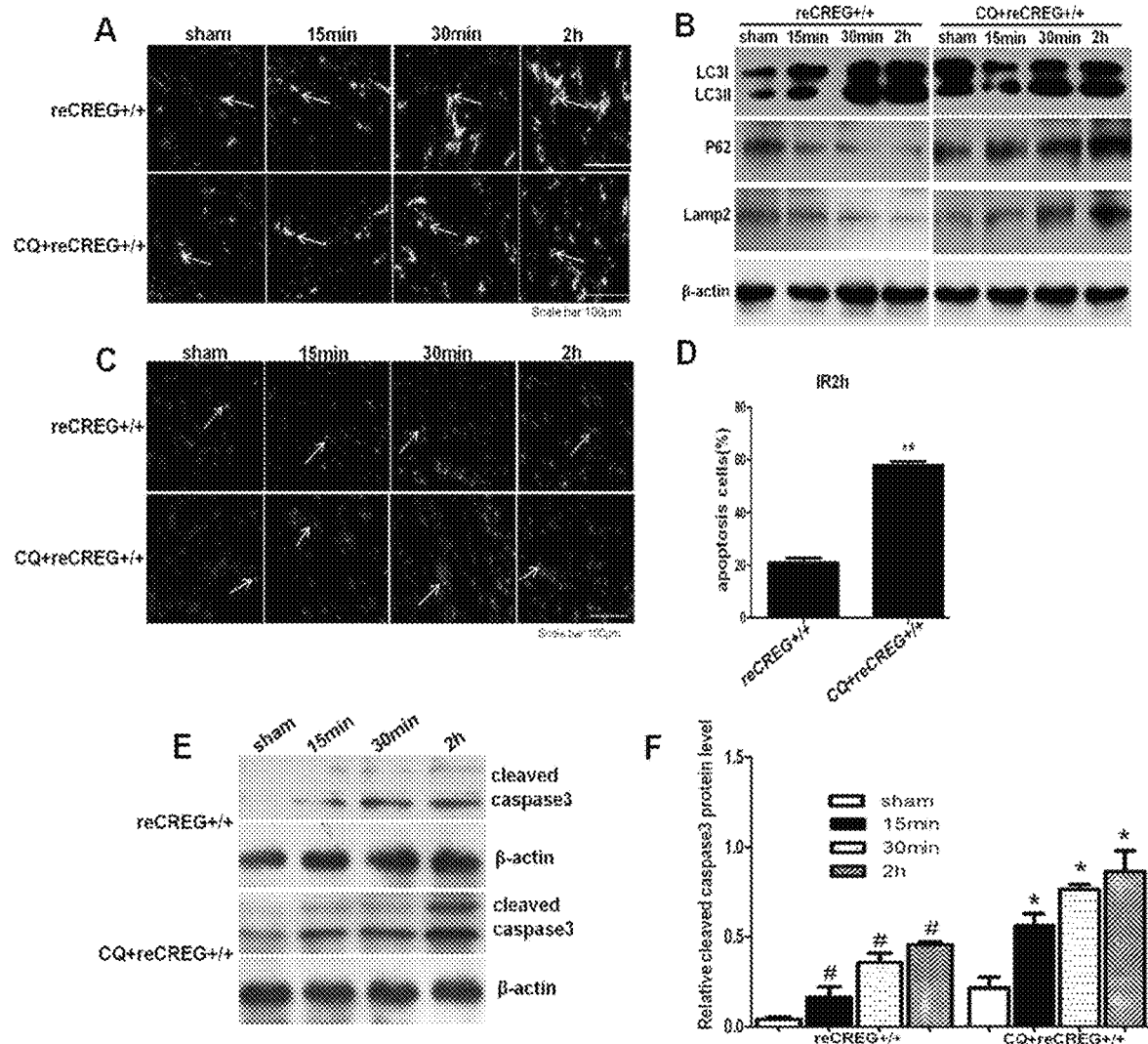

FIG. 8: Myocardial apoptosis and expression of autophagy protein was observed after administration of chloroquine (an autophagy inhibitor) in reCREG$^{+/+}$ mice after myocardial ischemia-reperfusion;

(A) Expression of autophagy protein LC3B in myocardium was detected by Immunofluorescence staining in the reCREG$^{+/+}$ mice and the reCREG$^{+/+}$ mice administrated with autophagy inhibitor chloroquine (reCREG$^{+/+}$+CQ);

(B) Expression of autophagy indicator proteins LC3, P62 and LAMP2 in myocardium of the mice of both groups was detected by Western blot;

(C-D) Myocardial apoptosis was detected by Tunel staining in the mice of both groups after myocardial ischemia-reperfusion;

(E-F) Expression of myocardial apoptosis protein cleaved caspase 3 was detected by Western blot in the mice of both groups.

Figure 9:
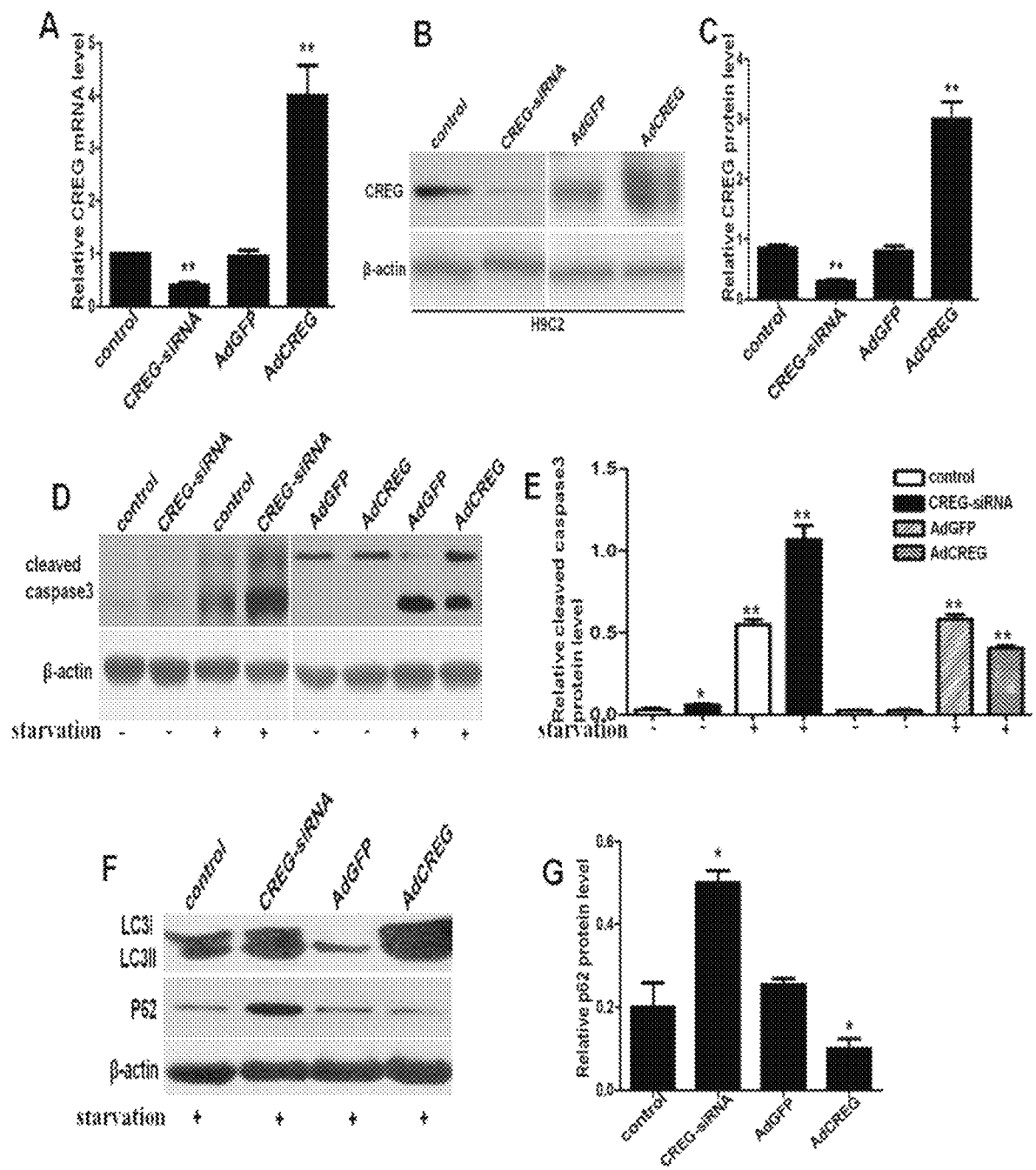

FIG. 9: Effect of CREG in regulation of autophagy to combat apoptosis and protect cardiomyocytes was observed in H9C2 cardiomyocyte line;

(A-C) Establishment of CREG low expression and over-expression models, i.e., transfecting H9C2 cells with siRNA and adenovirus, and detecting the transfection efficiency at RNA and protein levels;

(D-E) Inducing different cell groups by serum-starvation, and detecting expression of apoptosis protein cleaved caspase3 by Western blot;

(F-G) Expression of autophagy indicator proteins detected by Western blot in the above cells.

Figure 10:
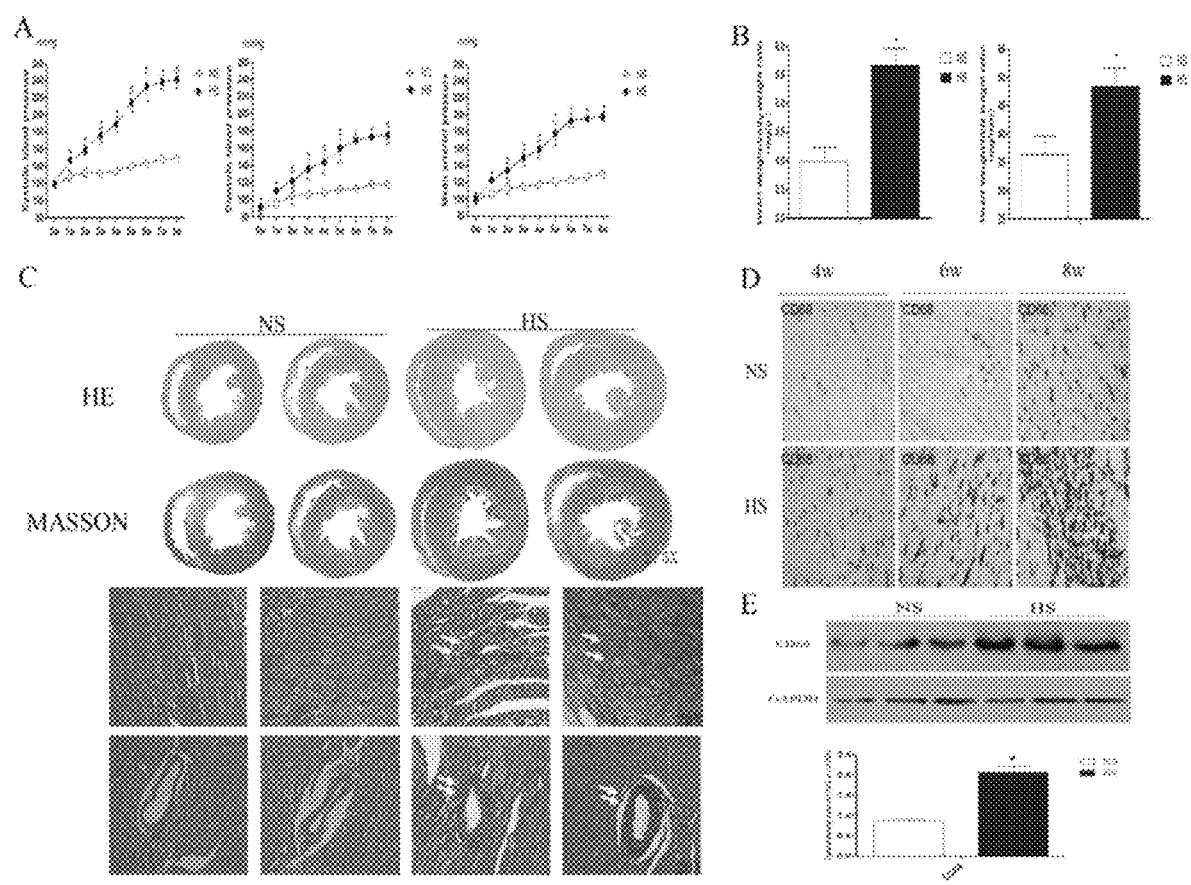

FIG. 10: Construction of salt-sensitive hypertension and myocardial fibrosis models in Dahl salt-sensitive rats by administrating with a high salt stress of 8% concentration;

(A) Systolic blood pressure, diastolic blood pressure and mean arterial pressure at different time points (1, 2, 3, 4, 5, 6, 7 and 8 weeks) after Dahl salt-sensitive rats being administrated with salt stress;

(B) ratio of heart weight/body weight, ratio of heart weight/tibia length of Dahl salt-sensitive rats at 8 week with salt stress s;

(C) General cardiac morphology and myocardial fibrosis detected by HE and Masson staining at 8 week with salt stress;

(D) Myocardial macrophage infiltration detected by Immunohistochemical staining at different time points (4, 6, 8 weeks) after being administrated with salt stress;

(E) Expression of CD68 protein in myocardial macrophages detected by Western blot at 8 week with salt stress.

Figure 11:
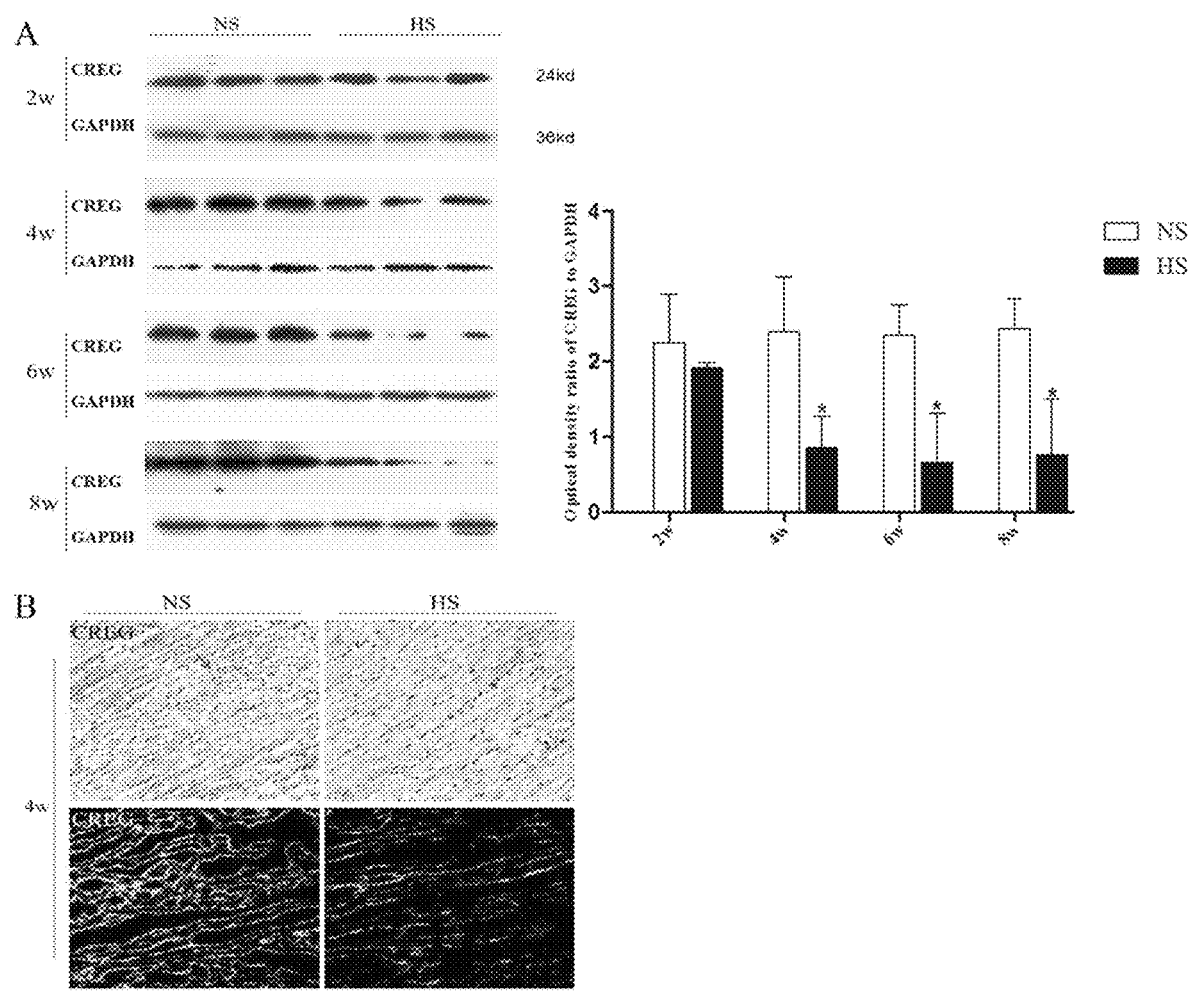

FIG. 11: Myocardial CREG protein expression in Dahl salt-sensitive rats after being administrated with high salt stress of 8%;

(A) Myocardial CREG protein expression detected by Western blot at different time points (2, 4, 6, 8 weeks) after being administrated with salt stress;

(B) Myocardial CERG expression detected by Immunohistochemistry and immunofluorescence staining at 4 week with salt stress.

Figure 12:
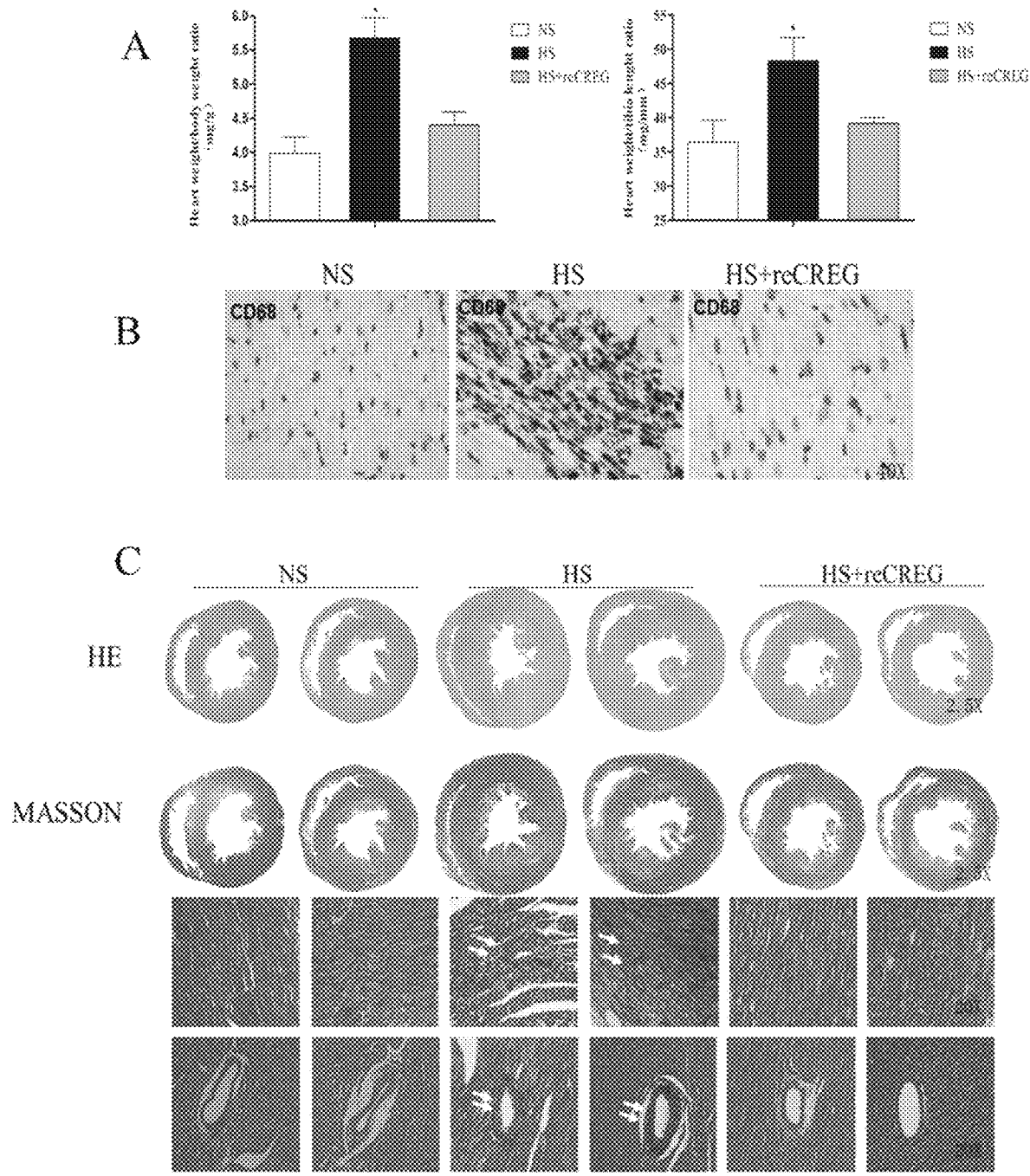

FIG. 12. Exogenously supplementing recombinant CREG protein improved myocardial fibrosis and cardiac inflammation after salt stress;

(A) Heart weight/body weight, ratio of heart weight/tibia length at 8 weeks of salt stress in rats of groups (normal salt group, high salt group, high salt+reCREG group) after exogenous supplementation of recombinant CREG protein;

(B) Macrophage infiltration detected by Immunohistochemical staining in rats of groups (normal salt group, high salt group, high salt+reCREG group) after exogenous supplementation of recombinant CREG protein;

(C) General cardiac morphology and myocardial fibrosis detected by HE and Masson staining in rats of groups (normal salt group, high salt group, high salt+reCREG group) after exogenous supplementation of recombinant CREG protein.

Figure 13:
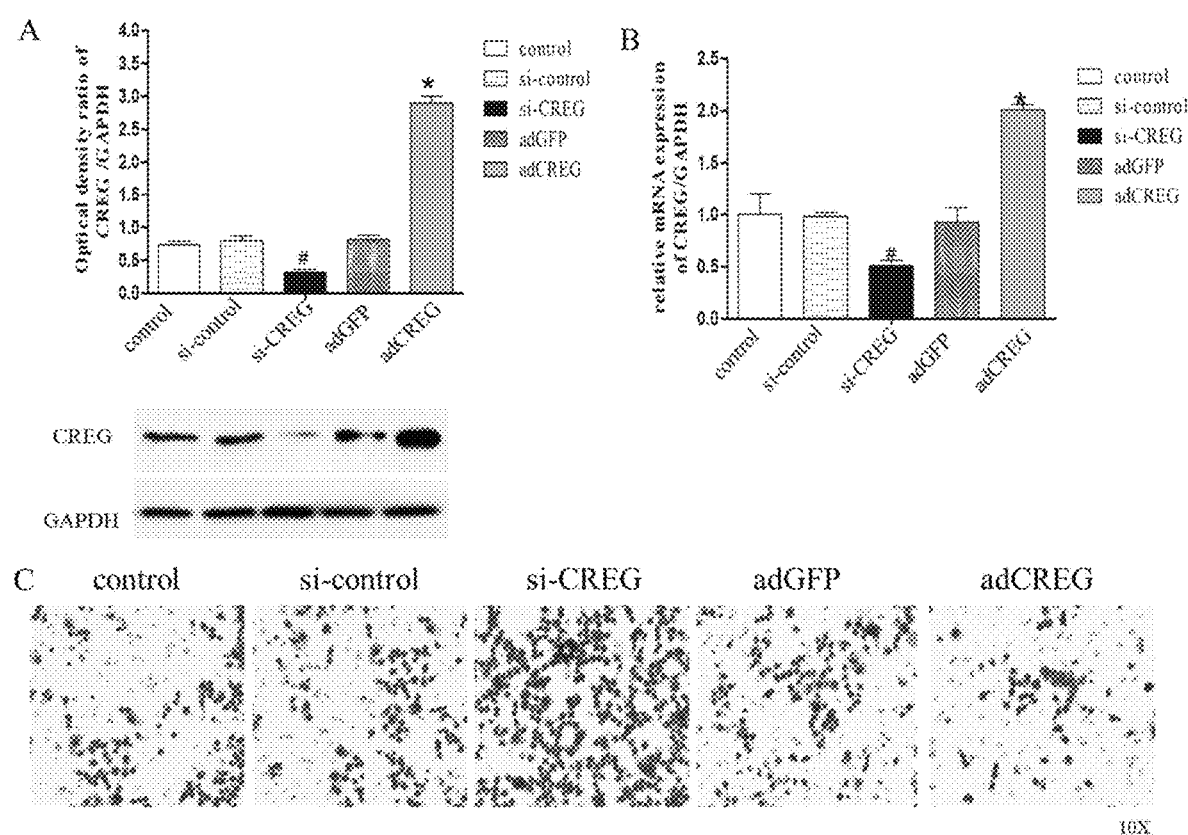

FIG. 13. Effect of CREG in combating inflammatory response and regulating myocardial fibrosis observed on Dahl salt-sensitive rat primary fibroblasts;

(A) Establishment of CREG low-expression and over-expression cell models, i.e., transfecting primary fibroblasts with siRNA and adenovirus with over-expression of CREG, and detecting transfection efficiency at protein level;

(B) Establishment of CREG low-expression and over-expression models, i.e., transfecting primary fibroblasts with siRNA and adenovirus with over-expression of CREG, and detecting transfection efficiency at mRNA level;

(C) Macrophage infiltration in fibroblasts detected by Transwell assay at CREG low-expression and over-expression group.

SPECIFIC MODEL FOR CARRYING OUT THE INVENTION

The embodiments of the present invention are described in detail below in conjunction with examples. However, those skilled in the art will understand that the following examples are only for illustrating the present invention, and should not be construed as limiting the scope of the present invention. In the examples, for those without specific conditions, conventional conditions or conditions suggested by manufacturers were applied. The used reagents or instruments without being specified with manufacturers are all commercially available conventional products.

The experimental data of the present invention are all percentages. The comparison between two sample rates were subjected to chi-square test, and statistical processing was performed by SPSS 17.0 software package. P<0.05 is statistically significant.

Example 1: Preparation of AMI Model in C57BL/6J Mice and Detection of CREG Expression in Myocardium at Different Time Points after AMI ① Establishment of AMI model in C57BL/6J MICE AMI model of mice was established by ligating anterior descending coronary artery. The instruments, materials and medicines were prepared before operation; mice were anesthetized with 3% chloral hydrate (450 mg/kg), and fixed on mouse plate in their supine position. Their tracheas were intubated, and connected with ventilator. Preoperative standard II lead ECG was measured and stored in the computer. The hair at chest operation area was cut off, then the skin, subcutaneous tissue, chest muscle and 3-4 cm of fascia were cut, the chest was opened, and the left anterior descending coronary artery was ligated at ⅓ up position with (6-0) suture. The appearance of height-increased and enlarged QRS wave indicated the successful ligation (S-T segment of ECG might not be necessarily visible), and penicillin in dose of 80 000 U/100 g was intramuscularly administered after surgery.

Results: According to the above experimental method, AMI model was prepared in mice, and height-increased and enlarged QRS wave appeared in ECG, suggesting AMI model was successfully prepared. The general cardiac morphology of the mice was observed at 7 day and 28 day after AMI, and the heart volume was obviously increased (see FIG. 1A).

② Observation of collagen content in myocardium of mice by Masson staining

1) Tissue pieces were drawn, fixed, embedded in paraffin, sectioned in 5 μm slices and dewaxed;
2) Washed with tap water and distilled water in order;
3) The paraffin slices were placed into Bouin's solution overnight;
4) Rinsed with water for 2-3 h, until the yellow disappeared completely;
5) Stained nucleus with Weigert iron hematoxylin solution for 20 min;
6) Rinsed with water for 30 seconds, differentiated with 1% ethanol hydrochloride;
7) Rinsed with water for 30 seconds, and returned back to blue with 0.2% ammonia;
8) Stained with Biebrich-Sdarlet-Acid for 15 min;
9) Rinsed with water for 30 seconds, stained with phosphoric acid solution for 2 min;
10) Shaken to remove phosphoric acid, without washing, directly stained with aniline blue liquid for 15 min;
11) Rinsed with water for 30 seconds, absolute ethanol for 10 seconds, absolute ethanol for 5 min;
12) Transparentized with xylene, mounted and fixed with neutral gum.

Figure 1:
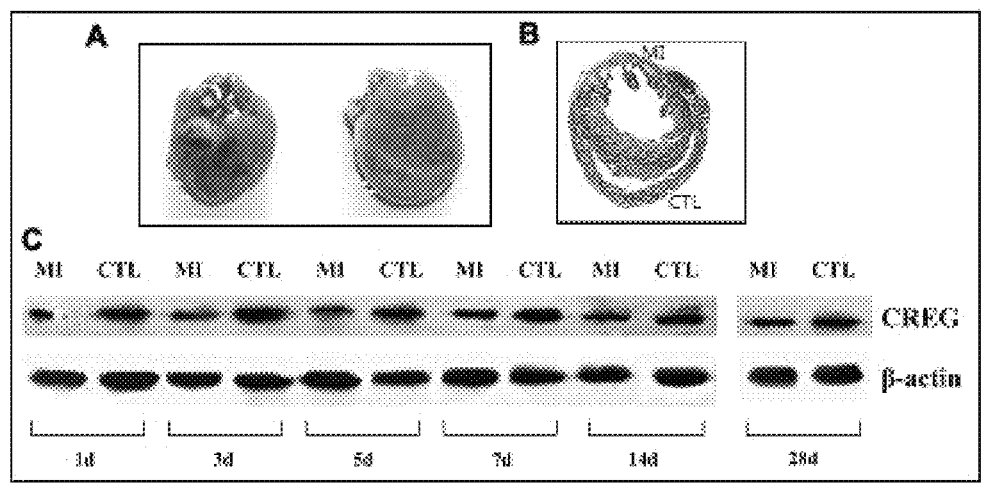
FIG. 1: Preparation of AMI model in wild-type C57BL/6J mice and detection of CREG protein in myocardium at different time points;
(A) General cardiac morphology of wild-type C57BL/6J mice, 7 days (left) and 28 days (right) after AMI;
(B) Masson staining of myocardial tissue in wild-type C57BL/6J mice, 28 days after AMI;
(C) CREG protein expression in myocardial infarction (MI) area and control area (CTL) of wild type C57BL/6J mice after AMI. was detected by Western blot at different time points (1, 3, 5, 7, 14 and 28 days).

The results showed that the collagen content in myocardium in C57BL/6J mice increased obviously at 28 days after AMI, which indicated that myocardial fibrosis occurred and ventricular remodeling appeared in the mice (see: FIG. 1B).

③ Western blot was used to detect the expression of CREG in myocardium in C57BL/6J mice at different time points after AMI.

In order to detect the CREG expression in myocardium of the mice, the proteins of myocardial necrosis zone, marginal zone and contralateral zone were extracted respectively, and the expression of CREG protein was detected by Western blot. BCA colorimetric kit was used to determine the protein concentration. After 50 μs of protein was boiled at 95° C. for 5 min, SDS-PAGE electrophoresis was performed on 12% separation gel to determine the termination time of electrophoresis. The sample was transferred to a cellulose membrane at a current of 350 mA for 45 min; after being blocked with 5% non-fat dry milk in TBS-T for 1.5 h at room temperature, the primary antibody was added and incubated overnight at 4° C. Respectively, 1:1000 anti-CREG antibody (Abcam, USA) and 1:1000 anti-beta-actin (Santa Cruz, USA) antibody were used as primary antibodies, goat-anti-mouse antibody labeled with horseradish peroxidase (Cell Signalling company, USA) was used as secondary antibody, Western blot detection was performed using ECL kit (Amersham, USA) for light-emitting development. Protein bands of about 24 KD and 43 KD in size were detected with CREG antibody and beta-actin antibody, respectively.

The results showed that the expression of CREG in myocardium of C57BL/6J mice was decreased rapidly in the early period (within 1 day) after AMI, and then gradually recovered, but did not return to the normal level at the later period of AMI (after 28 days) (see: FIG. 1C), suggesting that the expression of CREG protein in myocardium may be down-regulated after AMI, and exogenous supplementation of CREG may have a protective effect on cardiomyocytes during AMI.

Example 2: Establishment of CREG Heterozygote (CREG$^{+/-}$) Model in Mice with Low Expression of CREG, and CREG Expression Decreased in Myocardial Tissue of CREG$^{+/-}$ Mice ① CREG$^{+/-}$ mice preparation and genotyping.

CREG$^{+/-}$ knockout mice were established through the Shanghai Southern Model Animal Center. Methods: 2-3 exons of mouse CREG1 gene (Ensembl Gene ID: ENSMUSG000000111432) were deleted to cause mutation of CREG gene, resulting in the early termination of protein translation. Neo element was inserted between intron 1-2 and intron 3-4 (see FIG. 2A). The targeting vector used was CREG1-ABRFn-pBR322 plasmid (see FIG. 2B). PCR-Genotyping method was performed according to the following reaction system and reaction conditions for type identification.

1) 5' arm PCR identification: P1 Creg1-5P112-ATGTGCACAGTCATGGTTCTCC (SEQ ID NO: 1), P2 neo reverse-GGCCTACCCGCTTCCATTGCTC (SEQ ID NO: 2); amplification position was plasmid 17919-17940, fragment length was 3531 bp. PCR reaction conditions: 95° C. 4 min, 94° C. 45 s, 63.6° C. 210 s, 72° C. 10 min, 34 cycles.

2) 3' arm PCR identification: P3 neo-Lh-CCGTGCCTTCCTTGACCCTGG (SEQ ID NO: 3), P4 Creg1-3P216-GATGAACCTGGCGTCCAGCAC (SEQ ID NO: 4); amplification position was plasmid 23090-23110, fragment length was 1378 bp. PCR reaction conditions: 95° C. 4 min, 94° C. 45 s, 65.9° C. 330 s, 72° C. 10 min, 34 cycles.

PCR Reaction System: (25 μl)

| Reagent | Volume (μl) |
| --- | --- |
| ddH$_2$O | 16.0 |
| 10xBuffer | 2.5 |
| dNTP | 4.0 |

-continued

| Reagent | Volume (µl) |
|---|---|
| P1 or P3 | 0.5 |
| P2 or P4 | 0.5 |
| DNA* | 1.0 |
| LaTaq | 0.5 |

Figure 2:
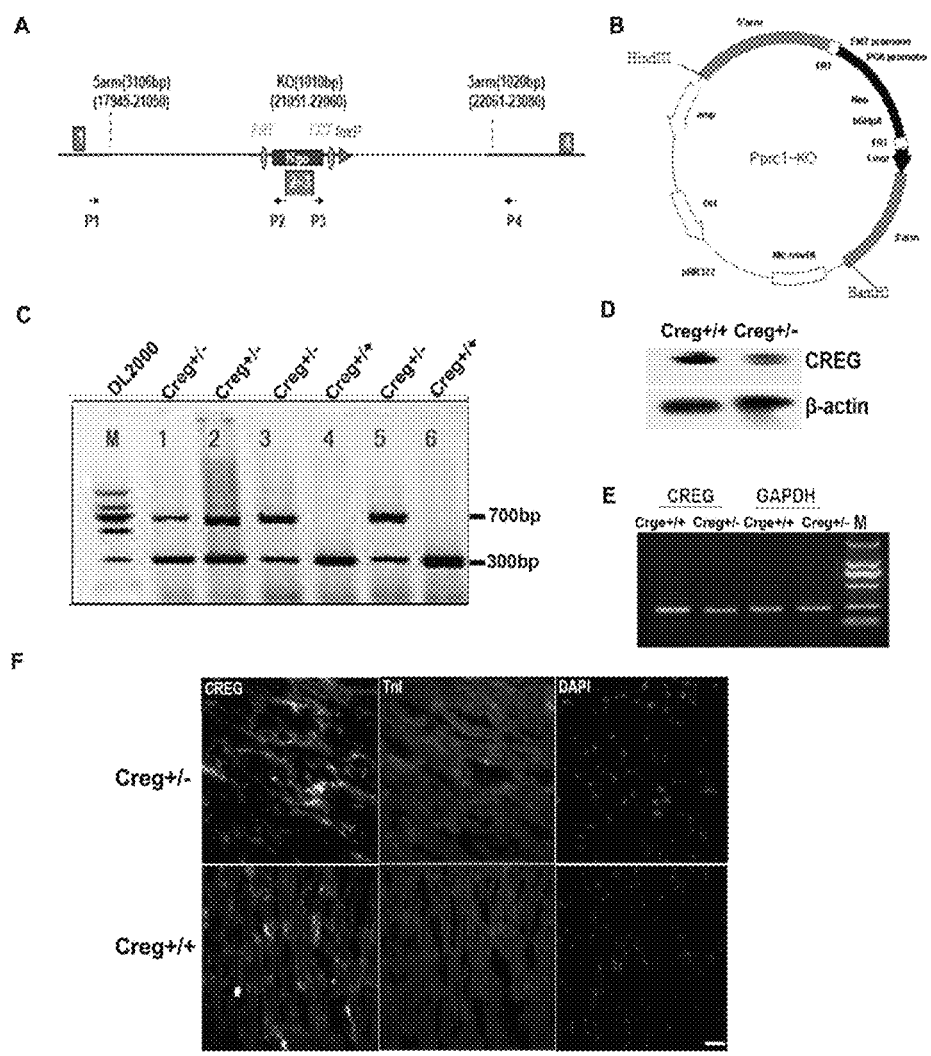
FIG. 2: Establishment of CREG heterozygote (CREG$^{+/-}$) mouse model with low CREG expression and detection of CREG expression in myocardial tissue;
(A) Schematic diagram of CREG$^{+/-}$ mouse model gene targeting fragments;
(B) Schematic diagram of CREG$^{+/-}$ mouse model gene targeting vector;
(C) Genotypes of CREG$^{+/-}$ mice and littermate wild-type CREG$^{+/+}$ mice were detected by RT-PCR genotyping method;
(D) CREG protein expression in myocardial tissues of CREG$^{+/-}$ mice and littermate wild-type CREG$^{+/+}$ mice was detected by Western blot;
(E) CREG mRNA expression in myocardial tissues of CREG$^{+/-}$ mice and littermate wild type CREG$^{+/+}$ mice was detected by RT-PCR;
(F) CREG expression in myocardial tissues of CREG$^{+/-}$ mice and littermate wild type CREG$^{+/+}$ mice was detected by Immunofluorescence staining method.

The results showed that all of the presently born mice were CREG$^{+/-}$ mice and CREG$^{+/+}$ wild type mice (i.e, littermate control group), and without CREG homozygous gene deletion mice (CREG$^{-/-}$), which suggested that CREG gene might play a very important role in mouse embryonic development (see FIG. 2C).

② Compared with the littermate control group, the CREG expression in myocardium of CREG$^{+/-}$ mice was significantly reduced.

Western blot, RT-PCR and tissue immunofluorescence staining methods were used to detect the expression of CREG in myocardium of CREG$^{+/-}$ mice and the littermate CREG$^{+/+}$ wild-type mice, respectively.

1) CREG protein expression levels was detected by Western blot method in myocardium of the mice of the littermate control group and the CREG$^{+/-}$ mice The specific method was the same as in Example 1.

The results showed that the CREG protein expression level in myocardium of the CREG$^{+/-}$ mice was significantly decreased in comparison with the mice of the littermate control group (see: FIG. 2D).

2) CREG mRNA levels in myocardium of the CREG$^{+/-}$ mice and the littermate CREG$^{+/+}$ wild-type mice was detected by RT-PCR a. Design of mouse CREG RT-PCR primer: the mouse CREG mRNA sequence (NM_011804.2) was queried in GenBank, and the mouse CREG gene RT-PCR primer was designed using the Primer Premier5.0 software and sent to and synthesized in Shanghai Sangon Biotech. The primer sequences were as follows:

| CREG upstream primer | GAGGAAGAGAGGTGCAGGTG (SEQ ID NO: 5) |
|---|---|
| CREG downstream primer | CATTGCTGTCCTCGACTGAA (SEQ ID NO: 6) |
| GAPDH upstream primer | AGAAGGCTGGGGCTCATTTG (SEQ ID NO: 7) |
| GAPDH downstream primer | AGGGGCCATCCACAGTCTTC (SEQ ID NO: 8) | b. Trizol extraction of total RNA from mouse myocardium: The myocardial tissue was lyophilized and pulverized in 100 cm mortar by adding liquid nitrogen, 1 mL of Trizol lysis buffer was added and stood at room temperature for 5 min; 200 µl of chloroform was added, mixed thoroughly, and stood at room temperature for 10 min; centrifugation at 12000 rpm/s for 10 min at 4° C. was performed, the supernatant was transferred to a clean centrifuge tube; 200 µl of isopropanol was added to the supernatant and mixed thoroughly; centrifugation at 12000 rpm/s for 10 min at 4° C. was performed, the supernatant was discarded; 1 ml of 75% ethanol was added to suspend deposit; centrifugation at 12000 rpm/s for 10 min at 4° C. was performed, the supernatant was discarded; 50 µl of RNase-Free deionized water was added to dissolve the deposit. After that, spectrophotometer and 1% agarose gel electrophoresis were used to detect RNA concentration, purity and integrity.

c. RT-PCR reaction: Total RNA extracted from mouse myocardium was reverse transcribed into cDNA (using cDNA first-strand synthesis kit of TakaRa; amplification conditions: 37° C. for 15 min, 85° C. for 5 s), and the mouse CREG coding sequence was amplified by the following reaction system and reaction conditions, and the fragment length was 250 bp.

Specific Reaction System and Conditions:

| Reagents | Volume (µl) |
|---|---|
| ddH$_2$O | 9.5 |
| 2 × Taq Master Mix | 12.5 |
| Upstream primer | 1 |
| Downstream primer | 1 |
| cDNA template | 1 |
| LaTaq | 0.5 |

Reaction conditions: 95° C., 3 min, 94° C., 30 s; 59° C., 30 s; 72° C., 1 min, 30 cycles, 72° C., 10 min.

The amplified products were separated and detected by 2% agarose gel electrophoresis, and the images were stored by gel imager.

The results showed the CREG mRNA level in myocardium of the CREG$^{+/-}$ mice showed a significant decrease in comparison with the mice of the littermate control group (see: FIG. 2E).

3) Expression of CREG in myocardium of the mice of the littermate control group and the CREG$^{+/-}$ mice was detected by tissue immunofluorescence staining method a. The freshly harvested mouse heart tissue was embedded in a frozen embedding material and frozen sectioned, with a thickness of 5 µm;

b. Fixed with 4% paraformaldehyde at room temperature for 20-30 min;

c. Sealed with goat serum at room temperature for 30 min;

d. Added with 1:100 anti-CREG antibody (Abcam, USA) and 1:100 anti-Troponin I (TNI) antibody (cardiomyocyte marker, Abcam, USA), placed in a wet box and stood at 4° C. overnight;

e. Washed with PBS three times, each 10 min;

f. Added with fluorescent labeled secondary antibody (1:100), and incubated at room temperature for 2 h in dark;

g. Washed with PBS three times, each 10 min;

h. Nuclei were stained with DAPI;

i. Mounted with 95% glycerol.

The results showed that in comparison with the mice of the littermate control group, the CREG expression in myocardium decreased significantly in the CREG$^{+/-}$ mice (the results were shown in FIG. 2F).

Example 3: In Comparison with the Mice of the Littermate Control Group, the CREG$^{+/-}$ Mice after AMI Showed a Significant Increase in Mortality, Significant Deterioration of Cardiac Contractile Function and Increased Ventricular Remodeling ① Establishment of AMI model in CREG$^{+/-}$ mice and littermate control group was same as in Example 1.

② Survival analysis after AMI in the CREG$^{+/-}$ mice and the mice of the littermate control group.

After AMI in mice, the number of dead mice was observed and recorded daily until the 28th day, and the survival curve was drawn.

Figure 3:
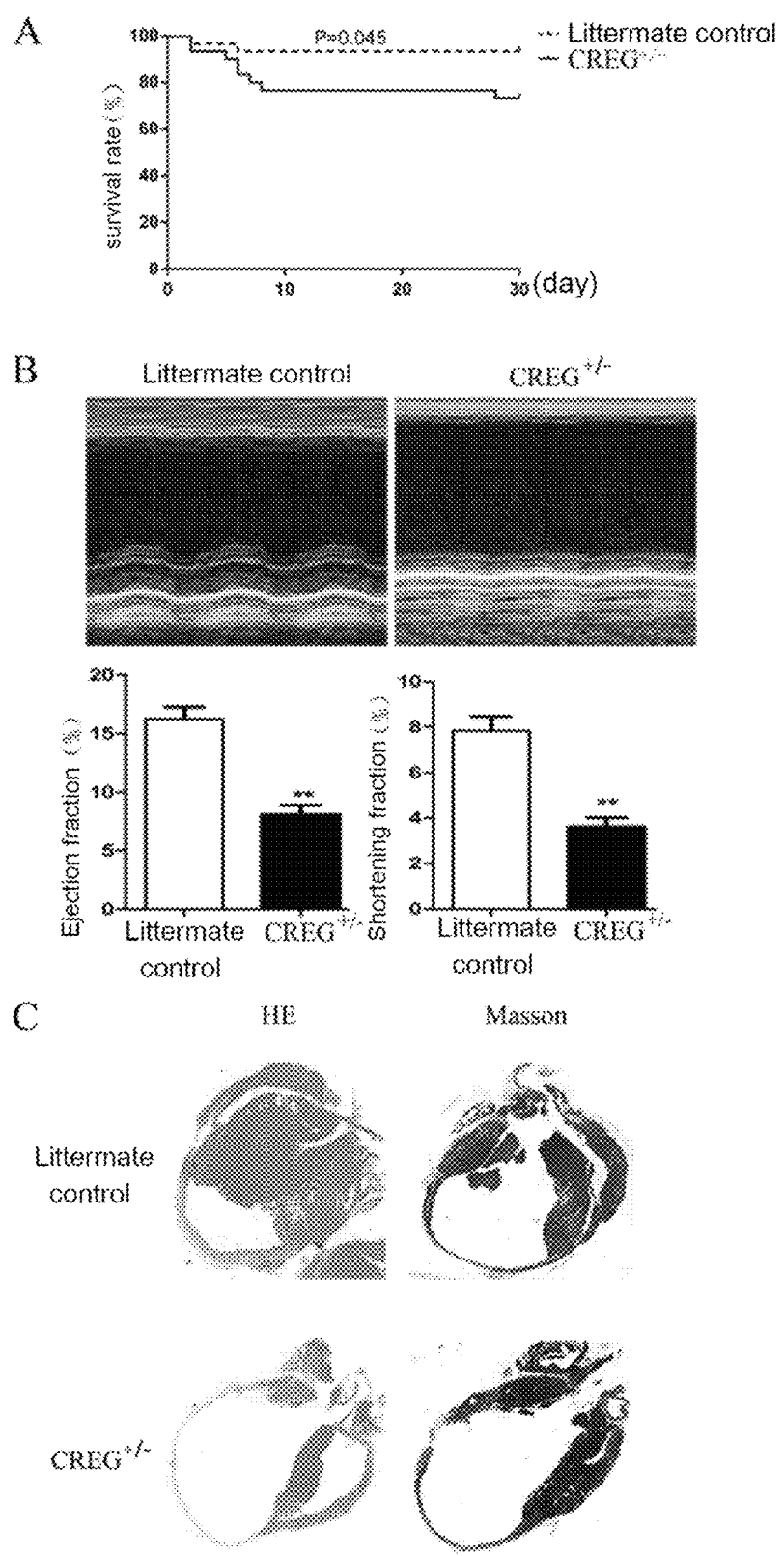
FIG. 3: Detection of cardiac systolic function and ventricular remodeling in CREG$^{+/-}$ mice and littermate wild-type CREG$^{+/+}$ mice at 28 days after AMI;
(A) Survival analysis of CREG$^{+/-}$ mice at 28 days after AMI surgery;
(B) Evaluation of cardiac systolic function by Small Animal ultrasonography in CREG$^{+/-}$ mice and littermate wild type CREG$^{+/+}$ mice 28 days after AMI;
(C) Evaluation of cardiac morphology and ventricular remodeling by HE staining and Masson staining in CREG$^{+/-}$ mice and littermate wild type CREG$^{+/+}$ mice 28 days after AMI.

The results showed a significant increase in mortality with 28 days after AMI in the CREG$^{+/-}$ mice compared to the mice of the littermate control group (see FIG. 3A for results).

③ Evaluation of cardiac systolic function in mice by small animal ultrasonography The mice were anesthetized with isoflurane and the cardiac contractile function was measured with a Vevo2100 type small animal cardiac ultrasonographer. ECG, respiration and other physiological parameters of mice were simultaneously recorded, the heart rate was maintained at about 450 beats/min and the heart rate was stabilized for 1 min, then a coupling agent was coated on chest for ultrasonography. Line M-type ultrasound and acquisition of images were performed, which were measured and analyzed by the heart function analysis software accompanied with the small animal ultrasonographer to obtain ejection fraction value and shortening fraction value.

The results showed that, compared with the littermate control group, the CREG$^{+/-}$ mice had significantly worse heart function at 28 days after AMI, with a significant decrease in ejection fraction and shortening fraction (see: FIG. 3B).

④ Observation of general cardiac morphology by HE in the CREG$^{+/-}$ mice and the littermate control group mice 28 days after AMI 1) Tissue material were drawn, fixed, paraffin embedded in conventional way, and sectioned into 5 μm slices;

2) The slices were deparaffinized with xylene and washed with ethanol at all levels: xylene (I) 5 min→xylene (II) 5 min→100% ethanol 2 min→95% ethanol 1 min→80% ethanol 1 min→75% ethanol 1 min→distilled water 2 min;

3) Stained with hematoxylin for 5 min, rinsed with tap water;

4) Differentiated with ethanol hydrochloride for 30 s;

5) Immersed in tap water for 15 min;

6) Placed in Eosin liquid for 2 min;

7) Conventionally dehydrated, and transparent mounted: 95% ethanol 1 min→95% ethanol 1 min→100% ethanol (I) 1 min→100% ethanol (II) 1 min→xylene (I) 1 min→xylene (II) 1 min→Neutral resin sealing.

⑤ Ventricular remodeling was observed by Masson staining in the CREG$^{+/-}$ mice and the littermate control group mice 28 days after AMI, and details could be seen in Example 1.

The results showed that, compared with the mice of the littermate control group, the ventricular wall thickness became significantly thinner, the ventricular cavity became larger, and the degree of ventricular fibrosis was significantly increased in the CREG$^{+/-}$ mice at 28 days after AMI (see: FIG. 3C).

Example 4: Exogenous Supplementation of Glycosylated CREG Protein and Non-Glycosylated CREG Protein could Significantly Increase Survival Rate and Cardiac Contractility Function, and Improve Ventricular Remodeling in C57BL/6J Mice at 28 Days after AMI ① Survival analysis of the C57BL/6J mice and the mice with exogenously supplemented with glycosylated and non-glycosylated CREG proteins was examined at 28 days after AMI.

The mice were divided into sham-operation group, C57BL/6J control group receiving AMI operation only, therapeutic groups in which mice were subcutaneously embedded with glycosylated CREG protein (Origene, USA, TP301654, in which the amino acids at positions 160,193 and 216 of CREG protein were glycosylated, 150 μg/kg·d), or administrated with non-glycosylated CREG protein (Abcam company, USA, ab131699, in which none of the amino acid site of CREG protein was glycosylated, 150 μg/kg·d). After AMI of mice, the number of dead mice was observed and recorded daily until the 28th day, and the survival curve was drawn. At the same time, the dead mice were autopsied and the cause of death was clarified.

The results showed that all of the mice in the sham operation group survived, while the survival rates in the mice of the glycosylated CREG protein group and the non-glycosylated CREG protein group were significantly higher than that in the C57BL/6J control group. In addition, the analysis of the death cause showed that the number of mice in the glycosylated and non-glycosylated CREG protein groups that died of pulmonary congestion were significantly lower than those in the C57BL/6J group, suggesting that the both groups had less heart failure than the control group (see FIG. 4A).

② The cardiac contractile function of the sham operation group, the C57BL/6J group, the glycosylated CREG protein group and the non-glycosylated CREG protein group was evaluated by small animal ultrasonography, and the details were the same as Example 3.

Figure 4:
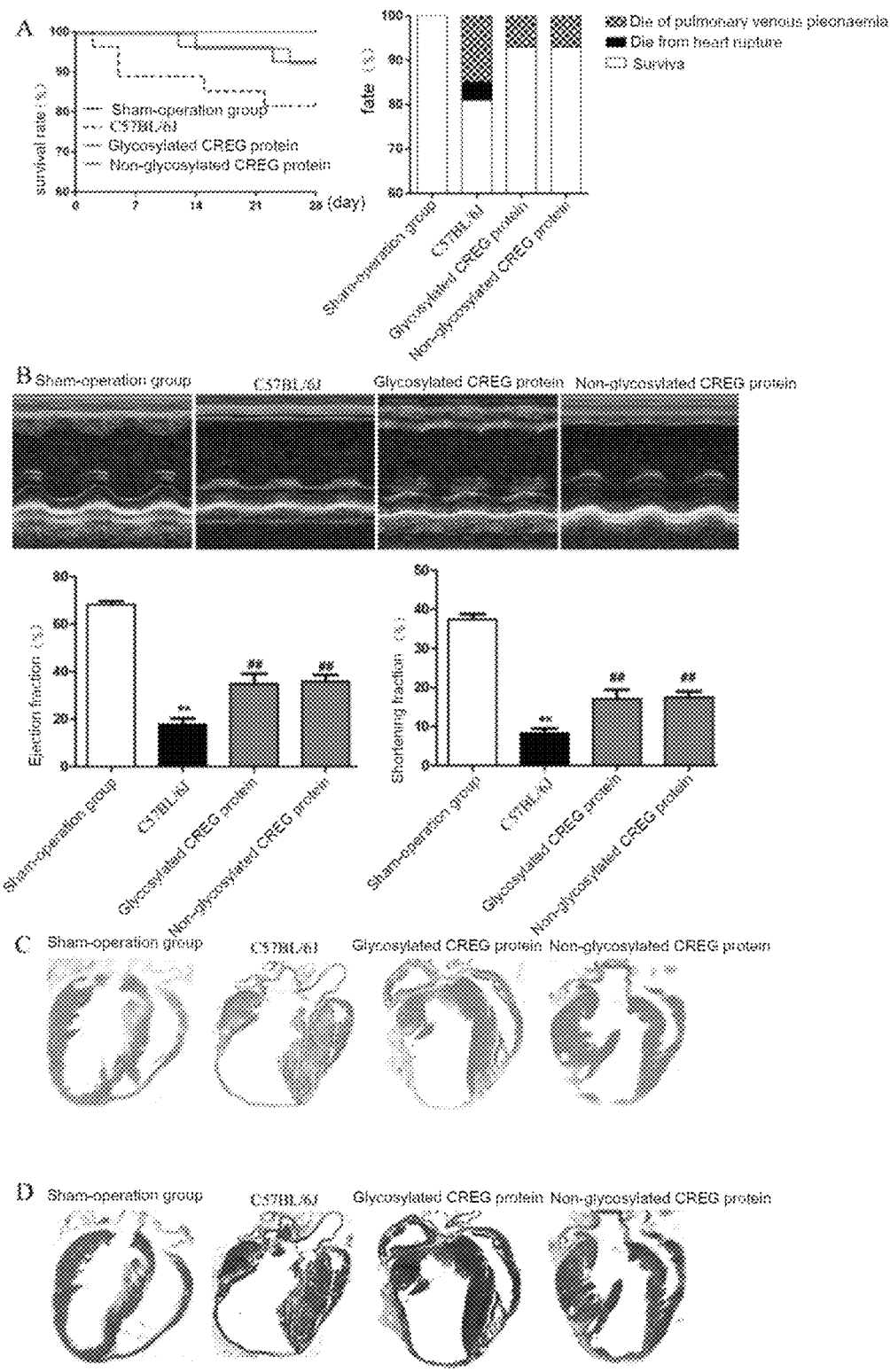
FIG. 4: Glycosylated and non-glycosylated CREG proteins significantly increased survival rate and cardiac contractility, and improved ventricular remodeling in CREG$^{+/+}$ mice 28 days after AMI;
(A) Mice were divided into sham-operation group, group of CREG$^{+/+}$ mice (C57BL/6J group) receiving AMI only, groups of CREG$^{+/+}$ mice being implanted subcutaneously with glycosylated and non-glycosylated CREG protein (150 μg/kg·d). Survival analysis and death cause analysis in the mice of these groups were performed at 28 days after AMI;
(B) Evaluation of cardiac contractile function performed by Small Animal ultrasonography in the mice of the sham-operation group, the C57BL/6J group, the glycosylated CREG protein group and the non-glycosylated CREG protein group at 28 days after AMI;
(C) Evaluation of general morphology of cardiac tissues by HE staining after AMI in the mice of the sham-operation group, the C57BL/6J group, the glycosylated CREG protein group and the non-glycosylated CREG protein group;
(D) Evaluation of ventricular remodeling by Masson staining at 28 days after AMI in the mice of the sham-operation group, the C57BL/6J group, the glycosylated CREG protein group and the non-glycosylated CREG protein group.

The results showed that in comparison with the sham operation group, the C57BL/6J mice after AMI had worse cardiac contractile function, and significantly decreased ejection fraction and shortening fraction. Compared with the C57BL/6J mice, the mice of both the glycosylated CREG protein group and non-glycosylated CREG protein group showed significantly improved cardiac contractile function and remarkably increased ejection fraction and shortening fraction at 28 days after AMI (results as shown in FIG. 4B).

③ The myocardium remodeling was observed by HE staining and Masson staining in the mice of each group at 28 day after AMI, in which the details were the same as Examples 1 and 3.

The results showed that compared to the sham-operation group, the C57BL/6J mice at 28 days after AMI showed more obvious ventricular remodeling, thinned ventricular wall, enlarged ventricular cavity, and significantly increased degree of ventricular fibrosis. Compared to the C57BL/6J group mice, the mice of the glycosylated and non-glycosylated CREG protein groups showed significantly improved ventricular remodeling, thickened ventricular wall (see FIG. 4C), and significantly alleviated ventricular fibrosis (see FIG. 4D), suggesting that the CREG over-expression could improve ventricular remodeling after AMI.

The above findings suggested that glycosylated and non-glycosylated CREG proteins were expected to be potent drugs for the treatment of AMI and/or heart failure after AMI.

Example 5: Application of Myocardial Ischemia-Reperfusion in Mice would Down-Regulate the Expression of CREG Protein in Myocardium ① Establishment of myocardial ischemia-reperfusion model in mice Instruments, materials and medicines were prepared before operation. The thoracotomy ligation of left anterior descending coronary artery comprised the following steps and methods: the skin at 2 mm left side of sternum was cut, the ribs were exposed by blunt dissection of muscle, the intercostal muscle was gently separated in the fourth intercostal space with eye scissors, the two ribs were repeatedly clamped with upward vascular clamp to reduce bleeding. The 3,4 ribs were cut, the chest wall was pulled open with a pull hook, and double strand ligatures were pulled through the chest wall muscles of both sides to left small circles inner side. The envelope was carefully cut, and the heart was gently pressed with a cotton swab. A needle was inserted at a position about 2 mm to the inferior margin of left aurcle with a needle deep of about 1.5 mm, the needle was withdrawn diagonally to the upper right direction of pulmonary artery cone, the needle spacing was about 2-3 mm, and the two ends of the ligatures passed through the small circles, respectively. The ligatures were temporarily kept without ligation. After being stabilized for 10 minutes, the ligatures were tighten, and ligated together with a small segment of polyethylene tube (for pressing blood vessels). ECG was immediately observed, and the appearance of height-increased and enlarged QRS wave was used as an indicator of successful ligation (change of S-T segment might not be visible, see the literature), and the time of ischemia was recorded. After 30 min, the ligatures were loosen to open the vascular for reperfusion, ECG was immediately observed, and the QRS wave should be decreased and narrowed after a few minutes.

② Detection of CREG mRNA levels after myocardial ischemia-reperfusion

C57BL/6 wild type ($CREG^{+/+}$) mice, $CREG^{+/-}$ mice, and wild type mice administrated with exogenous recombinant CREG protein (300 μg/kg·d) ($reCREG^{+/+}$) were respectively studied, and RT-PCR method was used to detect the expression of CREG in myocardium of mice. Myocardial tissues of $CREG^{+/+}$, $CREG^{+/-}$ and $reCREG^{+/+}$ mice were withdrawn, and added with 1 ml of Trizol lysis solution to extract total RNA of myocardium. According to the mouse CREG mRNA sequence (NM_011804.2) in GenBank, the mouse CREG gene RT-PCR primers were designed and synthesized as follows: Mouse CREG upstream primer: 5'-GAGGAAGAGAGGTGCAGGTG-3' (SEQ ID NO: 9), downstream primer: 5'-CATTGCTGTCCTCGACTGAA-3' (SEQ ID NO: 10); internal reference GAPDH upstream primer: 5'-AGAAGGCTGGGGCTCATTTG-3' (SEQ ID NO: 11), downstream primer: 5'-AGGGGCCATCCA CAGTCTTC-3' (SEQ ID NO: 12).

After cDNA was synthesized according to the extracted RNA (cDNA First Strand Synthesis Kit, TakaRa; Amplification conditions: 37° C., 15 min; 85° C., 5 s), the mouse CREG coding sequence with a total of 250 bases was amplified by the following reaction system and reaction conditions.

The amplified products were separated by 2% agarose gel and stained with EB. The myocardial tissue lysates of the $CREG^{+/-}$ and $CREG^{+/+}$ mice were detected to cDNA expression with bands of approximately 250 bp in size. The results suggest that the CREG expression in myocardium of the $CREG^{+/-}$ mice is significantly reduced in comparison with the $CREG^{+/+}$ mice and $reCREG^{+/+}$ mice (the results were shown in FIG. 5A-B).

③ CREG protein expression was detected by Western blot in myocardium of $CREG^{+/+}$, $CREG^{+/-}$ and $reCREG^{+/+}$ mice after myocardial ischemia-reperfusion.

Western blot was used to detect CREG protein expression in the $CREG^{+/+}$, $CREG^{+/-}$ and $reCREG^{+/+}$ mice. The myocardial tissues of the three groups were taken and lysed, the protein concentrations of in the lysates were determined by BCA colorimetric kit. 45 μs of protein was added to 4×Loading buffer, boiled at 95° C. for 5 min, and SDS-PAGE electrophoresis was performed by 10% separation gel to determine the electrophoresis termination time. The sample was transferred to a cellulose membrane with a current of 350 mA for a period of 80 min; after being blocked with 5% non-fat dry milk in TBS-T for 1.5 h at room temperature, the primary antibody (anti-CREG antibody, 1:1000, anti-β-actin antibody, 1:2000) was added and incubated overnight at 4° C.; on the next day, placed on a shaker and shaken for 30 minutes, then the membrane was washed with TBS-T for 3 times, each 15 min; a rabbit-anti-mouse secondary antibody (1:1000 dilution) was added, incubated at room temperature for 2 h, the membrane was washed with TBS-T for 4 times, each 20 min; and ECL chemiluminescence imaging was performed.

Figure 5:
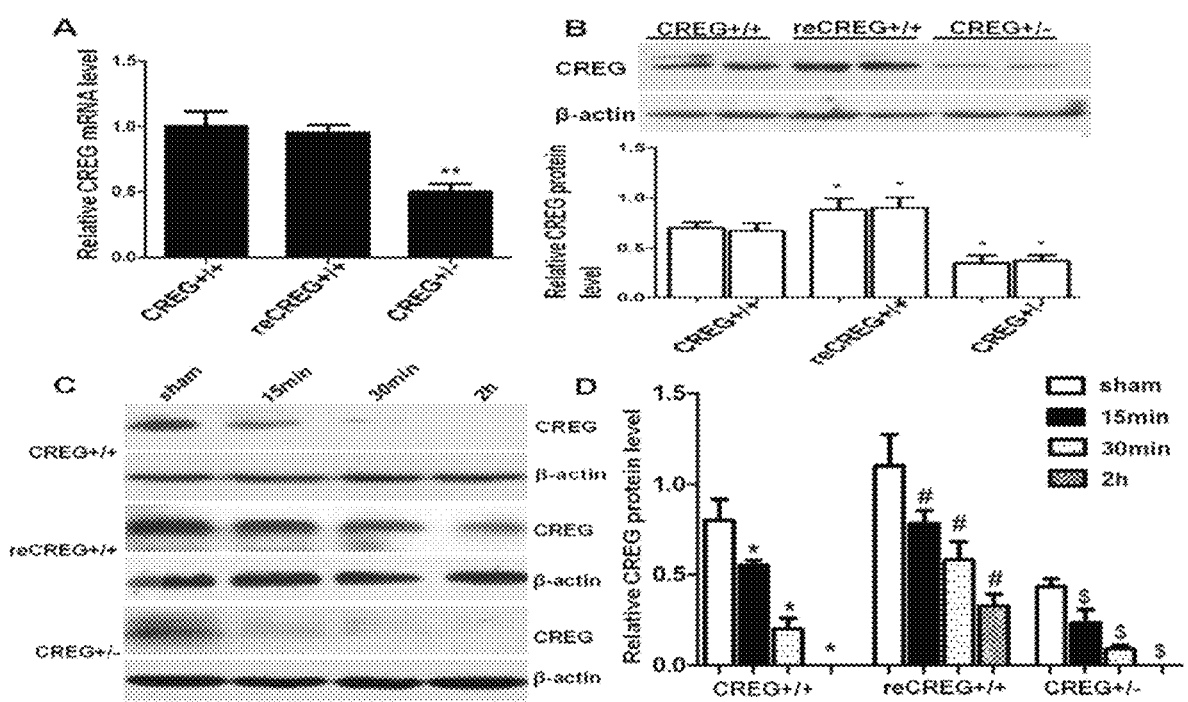
FIG. 5: Decrease of myocardial CREG protein expression during myocardial ischemia-reperfusion in CREG$^{+/+}$ mice;
(A) Without application of myocardial ischemia-reperfusion, CREG gene mRNA expression in myocardium was detected by RT-PCR in CREG$^{+/+}$ mice, mice administrated with exogenous CREG protein (reCREG$^{+/+}$), and CREG$^{+/-}$ mice;
(B) Without application of myocardial ischemia-reperfusion, CREG protein expression in myocardium was detected by Western blot in CREG$^{+/+}$ mice, reCREG$^{+/+}$ mice, and CREG$^{+/-}$ mice.

The results suggested that the expression of CREG protein gradually decreased with the extension of reperfusion time after myocardial ischemia-reperfusion, and such decrease is more obvious in the $CREG^{+/-}$ mice (see FIG. 5C-D).

Example 6: Changes in the Expression of CREG Protein in Mouse Myocardium can Affect Cardiac Function in Mice ① Comparison of cardiac function in the $CREG^{+/+}$ and $CREG^{+/-}$ mice at 28 days after myocardial ischemia-reperfusion. Vevo2100 ultrasound biomicroscopy system from VisualSonics of Canada was used, and the probe center frequency was 30 MHz. After the mice were anesthetized with 2% isoflurane, the hair of chest and abdomen was cut. The mice were fixed in supine position on a thermostat examination table and the temperature was kept at 37° C. The physiological parameters such as ECG and respiration of the mice were recorded synchronously. The heart rate was maintained at about 450 beats/min and the heart rate was stabilized for 1 min, then a coupling agent was coated on chest for ultrasonography. The results showed that at 28 days of myocardial ischemia-reperfusion, the $CREG^{+/-}$ mice had a significantly lowered cardiac function in comparison with the $CREG^{+/+}$ mice, whereas the mice administrated with exogenous recombinant CREG protein had a significantly improved cardiac function (the results were shown in FIG. 6A-C).

② Comparison of myocardial ischemic and necrosis in the $CREG^{+/+}$ mice, the $CREG^{+/-}$ mice and the mice administrated with exogenous recombinant CREG protein at 24 h after myocardial ischemia reperfusion.

The results of TTC staining suggested that the area of myocardial necrosis in the $CREG^{+/-}$ mice was significantly increased in comparison with the $CREG^{+/+}$ mice.

The above results showed that the expression of CREG protein was positively correlated with the cardiac function in mice during myocardial ischemia-reperfusion, in which the $CREG^{+/-}$ mice showed the lowest expression of CREG protein in myocardium and the worst cardiac function, while the mice administrated with exogenous recombinant CREG protein showed the highest level of CREG protein expression in myocardium and the best cardiac function (the results were shown in FIG. 6D-E).

Example 7: Administration of Exogenous Recombinant CREG Protein During Myocardial Ischemia-Reperfusion can Result in Decrease in Apoptosis of Cardiomyocytes in Mice, and Further Activation of Autophagy ① Tunel staining method was used to detect the cardiomyocytes apoptosis in $CREG^{+/+}$, $CREG^{+/-}$ and $reCREG^{+/+}$ mice. During Tunel staining, the reagents for staining were prepared, then the frozen tissue sections was placed in 4% paraformaldehyde and fixed at room temperature 10 min, washed with PBS for 2 times, each 10 min. After treatment with 3% hydrogen peroxide in methanol solution for 20 min, the sections were washed with PBS for 3 times, each 5 min, contacted with 0.1% sodium citrate for 2 min on ice; then Tunel staining solution was added to the sample surface, incubation was performed at 37° C. for 1 h in dark; washed with PBS, and nuclei stained with DAPI. The results suggested that the $CREG^{+/-}$ mice after myocardial ischemia-reperfusion exhibited the largest number of apoptotic cardiomyocytes, while the mice administrated with exogenous recombinant CREG protein exhibited the smallest number of apoptotic cardiomyocytes (the results were shown in FIG. 7A-B), indicating that CREG played a role of combating cardiomyocyte apoptosis.

② Western blot was used to detect the expression of apoptotic protein in myocardium. Western blot method was used to detect the expression of apoptosis indicator protein cleaved caspase 3 in myocardium of mice after myocardial ischemia-reperfusion. The results showed that the $CREG^{+/-}$ mice gave the highest of expression level of cleaved caspase 3 in myocardium, while the mice administrated with exogenous recombinant CREG protein gave the lowest expression level (the results were shown in FIG. 7C-D), which confirmed the results of Tunel staining and demonstrated again the effect of CREG protein on myocardial apoptosis.

③ Using immunofluorescence staining to observe the expression of autophagy protein LC3B in myocardium.

a. Frozen sections were allowed to dry at room temperature for 15 min;

b. The tissues to be stained were circled with a immunohistochemical oil pen, soak in PBS for 10 min to remove OCT;

c. The sections were blocked with PBS containing 10% normal serum for 1 h, without washing in this step, the blocking solution was just sucked out;

d. Rabbit-anti-mouse autophagy microtubule related protein light chain 3 (LC3B) monoclonal antibody (1:100) (purchased from Cell Signaling company, UK) was added and incubated overnight at 4° C.;

e. Washed with PBS for 3 times, each 10 min;

f. Added with fluorescence-labeled secondary antibody (1:100) (donkey-anti-rabbit Alex488 marker, Invitrogen, USA), incubated for 2 h at room temperature;

g. Washed with PBS for 3 times, each 15 min;

h. Mounted, and then observed and photographed the result with a fluorescence microscope.

The results showed that, in comparison with the $CREG^{+/+}$ mice, the LC3B expression in myocardium of the mice administrated with exogenous recombinant CREG protein at different phases of myocardial ischemia-reperfusion was significantly increased (the results were shown in FIG. 7E).

④ Using Western blot to detect autophagy protein expression in myocardium of the three kinds of mice.

Western blot was used to detect the expression of autophagy proteins in myocardium of three kinds of mice at different phases of myocardial ischemia-reperfusion. As a result, autophagy substrate protein P62 was found to accumulate in myocardium of the $CREG^{+/-}$ mice (the results were shown in FIG. 7F), suggesting the existence of an obstacle to autophagy. However, the autophagy was further activated in the mice administrated with exogenous recombinant CREG protein, suggesting that CREG promoted autophagy in myocardium during ischemia-reperfusion injury in mice.

Example 8. Lysosomal Inhibitor Chloroquine was Administered to Observe the Expression of Apoptosis and Autophagy Proteins in Myocardium ① Immunofluorescence staining was used to observe the expression of autophagy protein LC3B in myocardium.

Immunofluorescence staining showed that the expression of autophagy protein LC3B after myocardial ischemia-reperfusion was significantly increased in the mice administrated with chloroquine in comparison with the control group, suggesting that chloroquine inhibited the autophagy procedure and resulted in the accumulation of LC3B (the results were shown in FIG. 8A).

② Western blot was used to detect the expression of autophagy proteins in myocardium of the two kinds of mice.

Western blot was used to detect the expression of autophagy proteins in myocardium of the two kinds of mice at different phases of myocardial ischemia-reperfusion. As a result, it was found that autophagy function in the mice administrated with exogenous recombinant CREG protein was further activated, suggesting that CREG promoted the occurrence of autophagy (the results were shown in FIG. 8B).

③ Tunel staining was used to observe the cardiomyocytes apoptosis in the $reCREG^{+/+}$ mice and the $reCREG^{+/+}$+ CQ mice.

Tunel staining found that the mice administrated with both chloroquine and recombinant CREG protein showed a significantly increased number of apoptotic cardiomyocytes after myocardial ischemia-reperfusion in comparison with the mice administrated with only recombinant CREG protein (the results were shown in FIG. 8C-D).

④ Western blot was used to detect the expression of apoptosis-related protein cleaved-caspase3 in myocardium of the three groups of mice.

The results showed that the apoptotic protein cleaved caspase3 was increased in myocardium of the mice administrated with both chloroquine and recombinant protein simultaneously (the results were shown in FIG. 8E-F).

Example 9: Effect of CREG in Regulation of Autophagy to Combat Apoptosis and Protect Cardiomyocytes was Observed in H9C2 Cardiomyocyte Line ① To investigate the effect of CREG gene over-expression on CREG mRNA and protein expression in H9C2 cells, we first established a cell model overexpressing CREG gene. The preparation of recombinant adenovirus (Ad5-CREG) carrying human CREG gene was disclosed in Chinese Patent No. 200810000053.8 (Publication No. CN101475961A) which was deposited with the China Center for Type Culture Collection (CCTCC, Wuhan, Wuhan University) on Jan. 2, 2008, Accession No. CCTCC-V200801. The deposit information was disclosed in Chinese Patent CN 101475961A. The adenovirus expressing only GFP protein (Ad-GFP) served as a control. H9C2 cells were inoculated into culture flasks, and infected on the next day with Ad-CREG-GFP and Ad-GFP respectively at a multiplicity of infection (MOI) of 300, and the cells were harvested after 48 hours of culture for detection of CREG gene expression.

The cells transfected with Ad-CREG-GFP and Ad-GFP were collected, mRNA was extracted and reverse transcribed, RT-PCR was used to detect the expression of CREG gene, which details were the same as Example 1. As a result, the expression level of hCREG mRNA in the Ad-CREG- GFP group cells was significantly increased, suggesting that H9C2 cell model with over-expression of CREG gene was successfully established (the results were shown in FIG. 9A-C).

② The effect of CREG gene low-expression on the expression of CREG mRNA and protein in H9C2 was studied. Firstly, a CREG low-expression model was established by using CREG small interfering (siRNA) (SANTA CRUZ) and FuGENE HD Transfection Reagent (Promega) for 3 days, and the successful establishment of the model was verified by RT-PCR and Western blot (the results were shown in FIG. 9A-C).

③ The cells were treated with serum-starvation, and the apoptosis and autophagy in different groups were detected by Tunel staining and Western blot.

The results of Tunel staining and Western blot showed that the CREG low-expression group exhibited the largest number of apoptotic cells and the highest expression level of cleaved caspase3, while the CREG over-expression group exhibited the smallest number of apoptotic cells and the lowest expression level of cleaved caspase3 (FIG. 9D-E).

The results of Western blot showed that the autophagy proteins LC3A and P62 in the CREG low-expression group were significantly accumulated, suggesting that the autophagy function was inhibited, while the CREG over-expression group was further activated by autophagy; when lysosome inhibitor chloroquine was administrated on the basis of serum deprivation treatment of cells, the CREG over-expression group and the control group showed no significant difference in apoptosis and autophagy protein expression (the results were shown in FIG. 9F-G).

The results of the above studies suggested that the recombinant CREG protein was expected to become an effective drug for prevention or treatment of myocardial ischemia-reperfusion injury.

Example 10: Construction of Salt-Sensitive Hypertension and Myocardial Fibrosis Models in Dahl Salt-Sensitive Rats by Administrating with a High Salt Stress of 8%

① Construction of hypertension and myocardial fibrosis model in Dahl rats

Dahl rats were divided into normal salt group and high salt group, the normal salt group was given 0.3% normal salt diet, the high salt group was given 8% high salt diet; blood pressures were measured by in vitro rat tail blood pressure measurement method after 1, 2, 3, 4, 5, 6, 7 and 8 weeks of salt stress, and the rats were intraperitoneally anesthetized with 3% chloral hydrate (0.3 ml/100 g) at time point of 8 weeks. The hair of chest surgery area was cut, the skin was cut off, the chest was opened, the heart was removed, and the indicators such as heart weight, body weight, tibia length were measured.

The results showed that in comparison with the normal salt group, the high-salt group exhibited an increased blood pressure from 1 week after salt stress, which increased gradually with the extension of salt stress time, and gave a significant increase of blood pressure at time point of 8 weeks, suggesting the hypertension model was successfully established in salt-sensitive rats; when the heart was drawn at time point of 8 weeks, it was found that the ratio of heart weight/body weight, and the ratio of heart weight/tibia length were significantly increased (the results were shown in FIG. 10A-B).

③ General cardiac morphology and myocardial collagen content in Dahl rats of the normal salt group and the high salt group were observed by HE and Masson staining at time point of 8 weeks.

He Staining:
1) Tissue blocks were taken, fixed, paraffin embedded conventionally, and sectioned into 5 μm slices;
2) The slices were deparaffinized with xylene and washed with ethanol at all levels: xylene (I) 5 min→xylene (II) 5 min→100% ethanol 2 min→95% ethanol 1 min→80% ethanol 1 min→75% ethanol 1 min→distilled water 2 min;
3) Stained with hematoxylin for 5 min, rinsed with tap water;
4) Differentiated with ethanol hydrochloride for 30 s;
5) Immersed in tap water for 15 min;
6) Placed in Eosin solution for 2 min;
7) Conventionally dehydrated, transparent, mounted: 95% ethanol 1 min→95% ethanol 1 min→100% ethanol (I) 1 min→100% ethanol (II) 1 min→xylene (I) 1 min→xylene (II) 1 min→neutral resin sealed.

Masson Staining:
1) Tissue blocks were drawn, fixed, conventionally embedded in paraffin, sectioned into 5 μm sections and dewaxed;
2) Rinsed with tap water and distilled water in order;
3) The paraffin sections were placed in Bruin's solution overnight;
4) Rinsed with running water for 2-3 h, until the yellow disappeared completely;
5) Stained nucleus with Wiegert iron hematoxylin solution for 20 min;
6) Rinsed with running water for 30 s, differentiated with 1% ethanol hydrochloride;
7) Rinsed with running water for 30 s, returned back blue with 0.2% ammonia solution;
8) Stained with Biebrich-Sdarlet-Acid for 15 min;
9) Rinsed with running water for 30 s, stained with phosphoric acid solution for 2 min;
10) Shaken to remove phosphoric acid, without washing, directly stained with aniline blue liquid for 15 min;
11) Rinsed with running water for 30 s, absolute ethanol for 10 s, absolute ethanol for 5 min;
12) Transparentized with xylene, mounted and fixed with neutral gum.

The results showed that, in comparison with the normal salt group, the Dahl salt-sensitive rats at 8 weeks of high salt stress showed significant concentric hypertrophy, and the collagen content in myocardial interstitium and around coronary arteries were significantly increased (the results were shown in FIG. 10C), suggesting that obvious heart fibrosis occurred in Dahl salt-sensitive rats at 8 weeks of salt stress, i.e, ventricular remodeling occurred.

③ Myocardial macrophage infiltration at different time points was detected by immunohistochemical staining.
1) Paraffin sections were routinely dewaxed to water;
2) Heat repair: the sections were boiled in water at 100° C. for 40 min, closed and naturally cooled;
3) Endogenous peroxidase was blocked with hydrogen peroxide for 10 min; washed with PBS for 3 times;
4) Blocked with normal non-immune animal serum for 30 min at room temperature;
5) Removing serum and dropping the primary antibody: the serum was absorbed with filter paper, without washing, directly added dropwise with the primary antibody (1:100, Abcam, USA) for 2 h at room temperature (optionally, placed in 4° C. refrigerator overnight). Dropping the secondary antibody: if staying overnight, rewarmed for 30 min on the next day, washed with PBS for 3 times, added dropwise with 50 ul of biotinylated secondary antibody, and incubated at room temperature for 10 min;

6) Dropping streptavidin: washed with PBS for 3 times, added dropwise with 50 ul of peroxidase solution, incubated at room temperature for 10 min;

7) developed with DAB, observed under microscopy, timely terminated (terminated with tap water);

8) Counterstained with hematoxylin at room temperature for 5 min, rinsed with tap water;

9) Rinsed with tap water to return back blue, 5 min;

10) Dehydrated with gradient alcohol solutions, transparentized with xylene: I, II (xylene), each 15 min.

11) Mounted with neutral gum.

The results showed that there was a small amount of macrophage infiltration in myocardium of Dahl rats at 6 weeks after high salt stress for; and a large amount of macrophages were found in myocardium at 8 weeks in comparison with normal salt group (the results were shown in FIG. 10D), suggesting that inflammation was involved in pathological process of hypertensive myocardial fibrosis in salt-sensitive rats.

④ Western blot was used to detect the expression of macrophages in myocardium of rats in two groups at time point of 8 weeks of salt stress.

The BCA colorimetric kit was used to determine the protein concentration in lysates. After 50 μg of protein was boiled at 95° C. for 5 min, SDS-PAGE electrophoresis was performed on 12% separation gel to determine the termination time of electrophoresis. The sample was transferred to a cellulose membrane at a current of 350 mA for 45 min. After blocking with 5% skim milk powder diluted in TBS-T for 1.5 h at room temperature, the primary antibody was added and incubated overnight at 4° C. Respectively, 1:1000 anti-CREG antibody (Abcam, USA) and 1:1000 anti-beta-actin (Santa Cruz, USA) antibody were used as primary antibodies, goat-anti-mouse antibody labeled with horseradish peroxidase (Cell Signalling company, USA) was used as secondary antibody, Western blot detection was performed using ECL kit (Amersham, USA) for light-emitting development.

The results showed that, compared to the normal salt group, the expression of macrophage in the myocardium of the high salt group at 8 weeks of salt stress was significantly increased (results shown in FIG. 10E), suggesting that macrophage infiltration was involved in the pathological process of hypertensive myocardial fibrosis after salt stress.

Example 11: Myocardial CREG Protein Expression in Dahl Salt-Sensitive Rats after being Administrated with 8% High Salt Stress ① Western blot was used to detect the myocardial CREG protein expression in rats of two groups at different time points of salt stress.

The results showed that the CREG protein levels of the Dahl salt-sensitive rats under high salt stress at different time points (2, 4, 6, 8 weeks, respectively) were detected, in comparison with the normal salt group rats, the myocardial CREG protein level in the high salt group rats was significantly down-regulated from 4 weeks of salt stress, which continued to 8 weeks (the results were shown in FIG. 11A), suggesting that CREG protein expression was down-regulated in the pathological process of hypertensive myocardial fibrosis in salt-sensitive rats, that is, CREG protein was negatively correlated with the pathological process of hypertensive myocardial fibrosis.

② Immunohistochemical staining was used to detect the expression of CREG in myocardium of the two groups rats at time point of 4 weeks.

③ Immunofluorescence staining was used to detect the expression of CREG in myocardium of the two groups at time point of 4 weeks.

1) Freshly drawn cardiac tissues were embedded and fixed in frozen embedding agent and frozen sectioned into sections with thickness of 5 μm;

2) Fixed with 4% paraformaldehyde at room temperature for 20-30 min;

3) Blocked with goat serum at room temperature for 30 min;

4) Added with 1:100 anti-CREG antibody (Abcam company, USA), placed in a wet box, stood overnight at 4° C.;

5) Washed with PBS for 3 times, each 10 min;

6) Added with fluorescent labeled secondary antibody (1:100) and incubated in dark for 2 h at room temperature;

7) Washed with PBS for 3 times, each 10 min;

8) Nucleus stained with DAPI;

9) Mounted with 95% glycerol.

The results showed that the expression of CREG protein was significantly down-regulated in Dahl rats after high salt stress, suggesting that CREG protein expression was down-regulated during the pathological process of hypertensive myocardial fibrosis in salt-sensitive rats (see FIG. 11B).

Example 12: Exogenously Supplementing Recombinant CREG Protein Improved Myocardial Fibrosis and Cardiac Inflammation after Salt Stress ① Exogenous over-expression of recombinant CREG protein inhibited the ratio of heart weight/body weight and the ratio of heart weight/tibia length.

The results showed that after administration of exogenous recombinant CREG protein, the Dahl rats after salt stress were able to effectively suppress the ratio of heart weight/body weight and the ratio of heart weight/tibia length (see FIG. 12A), suggesting that recombinant CREG protein could effectively inhibit cardiac remodeling in Dahl salt-sensitive rats after salt stress.

② Immunohistochemical staining was used to detect macrophage infiltration in myocardial tissue of Dahl rats administrated with exogenous overexpressed recombinant CREG protein after salt stress.

The results showed that the macrophage infiltration in myocardium of the Dahl rats administrated with exogenous recombinant CREG protein were significantly reduced after salt stress (see FIG. 12B), suggesting that over-expression of CREG protein could effectively inhibit the macrophage infiltration in myocardium of the Dahl rats after salt stress.

③ Using HE and Masson staining to detect the effect of exogenous over-expressed recombinant CREG protein on the myocardial fibrosis and remodeling in Dahl rats after salt stress.

The results showed that after being administrated with exogenous recombinant CREG protein, the Dahl rats after salt stress exhibited significant improvement in cardiac concentric hypertrophy, and a significant reduction in both myocardial interstitium and perivascular collagen (see FIG. 12C), suggesting that CREG protein could effectively inhibit the myocardial fibrosis of Dahl rats after salt stress.

Example 13: Effect of CREG in Combating Inflammatory Response and Regulating Myocardial Fibrosis was Observed at Level of Dahl Salt-Sensitive Rat Primary Fibroblasts ① In order to investigate the effect of CREG gene over-expression on CREG mRNA and protein expression in Dahl primary fibroblasts, we first established a cell model overexpressing CREG gene. The preparation of recombinant adenovirus (Ad5-CREG) carrying human CREG gene was disclosed in Chinese Patent No. 200810000053.8 (Publication No. CN101475961A), which was deposited with the China Center for Type Culture Collection (CCTCC, Wuhan, Wuhan University) on Jan. 2, 2008, Accession No. CCTCC-V200801. The deposit information was disclosed in Chinese Patent CN 101475961A. Adenoviruses expressing only GFP protein (Ad-GFP) served as a control. Primary fibroblasts were seeded in culture flasks, infected on the next day with Ad-CREG-GFP and Ad-GFP respectively at a multiplicity of infection (MOI) of 300. After 48 hours of culture, cells were harvested and examined for CREG gene expression.

After Ad-CREG-GFP and Ad-GFP transfected cells were collected, mRNA and protein were extracted and RT-PCR and Western blot were used to detect whether the CREG over-expression model was successfully established. The Western blot method was the same as Example 1, and the RT-PCR method was as follows:

a. Design of rat CREG RT-PCR primers: The rat CREG mRNA sequence (NM_001105966.1) was queried in GenBank, and RT-PCR primers of rat CREG gene were designed by using the Primer Premier 5.0 software, sent to and synthesized in Shanghai Bioengineering Co., Ltd. The primer sequences were as follows:

b. Trizol extraction of total RNA from primary fibroblasts of rat myocardium: primary fibroblasts of each group in culture dish were added with 1 mL of Trizol lysis buffer, stood at room temperature for 5 min; added with 200 µl of chloroform, mixed thoroughly, stood at room temperature for 10 min; centrifuged at 12000 rpm/s for 10 min at 4° C., the supernatant was transferred to a clean centrifuge tube; 200 µl of isopropanol was added to the supernatant and mixed thoroughly; centrifuged at 12000 rpm/s for 10 min at 4° C., the supernatant was discarded; added with 1 ml of 75% ethanol to suspend the deposit; centrifuged at 12,000 rpm/s for 10 min at 4° C., the supernatant was discarded; added with 50 µl of RNase-Free deionized water to dissolve the deposit. After that, spectrophotometer and 1% agarose gel electrophoresis were used to detect RNA concentration, purity and integrity.

c. RT-PCR reaction: the extracted total RNA was reverse transcribed into cDNA (using cDNA first-strand synthesis kit from TakaRa, amplification conditions: 37° C. for 15 min; 85° C. for 5 s), and the rat CREG coding sequence was amplified by the following reaction system and reaction conditions, and the fragment length was 250 bp.

Specific Reaction System and Conditions:

| Reagent | Volume (µl) |
|---|---|
| ddH$_2$O | 9.5 |
| 2 × Taq Master Mix | 12.5 |
| Upstream primer | 1 |
| Downstream primer | 1 |
| cDNA template | 1 |
| LaTaq | 0.5 |

Reaction conditions: 95° C., 3 min; 94° C., 30 s; 59° C., 30 s; 72° C., 1 min; 30 cycles; 72° C., 10 min.

The amplified products were separated and detected by 2% agarose gel electrophoresis, and the images were stored by gel imager.

The results showed that CREG mRNA expression and protein levels were significantly increased in cells of the Ad-CREG-GFP group (FIG. 13A-B), suggesting that the primary fibroblast cell model with over-expression of CREG gene was successfully established.

② Effect of low-expression of CREG gene on CREG mRNA and protein expression in primary fibroblasts. Firstly, a model of low-expression of CREG was established, by using CREG small interfering (siRNA) (SANTA CRUZ) and FuGENE HD Transfection Reagent (Promega) for 3 days, and RT-PCR and Western blot was used to detect whether the model was successfully established.

The results showed that the CREG mRNA expression and protein levels were significantly decreased in the cells of the si-CREG group (FIG. 13A-B), suggesting the primary fibroblast model with low-expression of CREG gene was successfully established.

③ Transwell experiments were used to detect the effects of different groups of cells on the migration of macrophages.

The results showed that the macrophage infiltration was significantly increased in the primary fibroblasts treated with low-expressed CREG (the si-CREG group); however, the macrophage infiltration was significantly inhibited in the primary fibroblasts treated with over-expressed CREG (the results were shown in FIG. 13C), suggesting the over-expression of CREG could inhibit macrophage infiltration.

The above results suggested that recombinant CREG protein was expected to become an effective drug for prevention or treatment of myocardial fibrosis in salt-sensitive people.

Although specific embodiments of the present invention have been described in detail, those skilled in the art will understand, and various modifications and substitutions to those details may be made in accordance with all the teachings disclosed, and all of which are within the scope of the invention. The full scope of the invention is given by the appended claims and any equivalents thereof.

What is claimed is:

1. A method of treatment of acute myocardial infarction; heart failure after acute myocardial infarction; or myocardial ischemia-reperfusion injury, comprising administering to a subject in need thereof an effective amount of a human Cellular Repressor of E1A-stimulated Genes (CREG) protein.

2. The method according to claim 1, wherein the human CREG protein is a glycosylated protein or a non-glycosylated protein.

3. The method according to claim 2, wherein the glycosylated protein is TP301654, wherein the amino acids at positions 160, 193, and 216 of the human CREG protein are glycosylated.

* * * * *

SEQUENCE LISTING

<160> NUMBER OF SEQ ID NOS: 12

<210> SEQ ID NO 1
<211> LENGTH: 22
<212> TYPE: DNA
<213> ORGANISM: Artificial sequence
<220> FEATURE:
<223> OTHER INFORMATION: Synthesized primer

<400> SEQUENCE: 1
atgtgcacag tcatggttct cc                                            22

```
<210> SEQ ID NO 2
<211> LENGTH: 22
<212> TYPE: DNA
<213> ORGANISM: Artificial sequence
<220> FEATURE:
<223> OTHER INFORMATION: Synthesized primer

<400> SEQUENCE: 2
ggcctacccg cttccattgc tc                                              22

<210> SEQ ID NO 3
<211> LENGTH: 21
<212> TYPE: DNA
<213> ORGANISM: Artificial sequence
<220> FEATURE:
<223> OTHER INFORMATION: Synthesized primer

<400> SEQUENCE: 3
ccgtgccttc cttgaccctg g                                               21

<210> SEQ ID NO 4
<211> LENGTH: 21
<212> TYPE: DNA
<213> ORGANISM: Artificial sequence
<220> FEATURE:
<223> OTHER INFORMATION: Synthesized primer

<400> SEQUENCE: 4
gatgaacctg gcgtccagca c                                               21

<210> SEQ ID NO 5
<211> LENGTH: 20
<212> TYPE: DNA
<213> ORGANISM: Artificial sequence
<220> FEATURE:
<223> OTHER INFORMATION: Synthesized primer

<400> SEQUENCE: 5
gaggaagaga ggtgcaggtg                                                 20

<210> SEQ ID NO 6
<211> LENGTH: 20
<212> TYPE: DNA
<213> ORGANISM: Artificial sequence
<220> FEATURE:
<223> OTHER INFORMATION: Synthesized primer

<400> SEQUENCE: 6
cattgctgtc ctcgactgaa                                                 20

<210> SEQ ID NO 7
<211> LENGTH: 20
<212> TYPE: DNA
<213> ORGANISM: Artificial sequence
<220> FEATURE:
<223> OTHER INFORMATION: Synthesized primer

<400> SEQUENCE: 7
agaaggctgg ggctcatttg                                                 20

<210> SEQ ID NO 8
<211> LENGTH: 20
<212> TYPE: DNA
<213> ORGANISM: Artificial sequence
<220> FEATURE:
<223> OTHER INFORMATION: Synthesized primer
```

```
<400> SEQUENCE: 8
aggggccatc cacagtcttc                                           20

<210> SEQ ID NO 9
<211> LENGTH: 20
<212> TYPE: DNA
<213> ORGANISM: Artificial sequence
<220> FEATURE:
<223> OTHER INFORMATION: Synthesized primer

<400> SEQUENCE: 9
gaggaagaga ggtgcaggtg                                           20

<210> SEQ ID NO 10
<211> LENGTH: 20
<212> TYPE: DNA
<213> ORGANISM: Artificial sequence
<220> FEATURE:
<223> OTHER INFORMATION: Synthesized primer

<400> SEQUENCE: 10
cattgctgtc ctcgactgaa                                           20

<210> SEQ ID NO 11
<211> LENGTH: 20
<212> TYPE: DNA
<213> ORGANISM: Artificial sequence
<220> FEATURE:
<223> OTHER INFORMATION: Synthesized primer

<400> SEQUENCE: 11
agaaggctgg ggctcatttg                                           20

<210> SEQ ID NO 12
<211> LENGTH: 20
<212> TYPE: DNA
<213> ORGANISM: Artificial sequence
<220> FEATURE:
<223> OTHER INFORMATION: Synthesized primer

<400> SEQUENCE: 12
aggggccatc cacagtcttc                                           20
```